United States Patent
Rezai et al.

(10) Patent No.: US 6,878,647 B1
(45) Date of Patent: Apr. 12, 2005

(54) ELASTIC LAMINATE INCLUDING NONWOVEN LAYER FORMED FROM HIGHLY-ORIENTED-COMPONENT FIBERS AND DISPOSABLE GARMENT EMPLOYING THE SAME

(75) Inventors: Ebrahim Rezai, Kobe (JP); Yoko Mizutani, Ashiya (JP); Kazuyuki Ohnishi, Takaishi (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/806,047

(22) PCT Filed: Sep. 28, 1999

(86) PCT No.: PCT/US99/22471

§ 371 (c)(1),
(2), (4) Date: Mar. 26, 2001

(87) PCT Pub. No.: WO00/20206

PCT Pub. Date: Apr. 13, 2000

(30) Foreign Application Priority Data

Oct. 2, 1998 (WO) .............................. PCT/US98/21012
Oct. 2, 1998 (WO) .............................. PCT/US98/21013

(51) Int. Cl.[7] ........................... B32B 18/00; D04H 1/00
(52) U.S. Cl. ..................... 442/18; 442/328; 442/329; 442/327; 264/288.8; 604/396
(58) Field of Search .................... 264/288.8; 604/396; 442/327

(56) References Cited

U.S. PATENT DOCUMENTS

| 4,610,681 | A | | 9/1986 | Strohbeen et al. |
| 4,940,464 | A | | 7/1990 | Van Gompel et al. |
| 5,143,679 | A | | 9/1992 | Weber et al. |
| 5,156,793 | A | | 10/1992 | Buell et al. |
| 5,167,897 | A | | 12/1992 | Weber et al. |
| 5,171,239 | A | | 12/1992 | Igaue et al. |
| 5,789,065 | A | * | 8/1998 | Haffner et al. ............... 428/152 |
| 6,231,976 | B1 | * | 5/2001 | Dean et al. .................. 428/373 |

FOREIGN PATENT DOCUMENTS

| JP | 3-158236 | 7/1991 |
| JP | 03-158236 | 7/1991 |
| WO | WO93/17648 | 9/1993 |
| WO | WO99/48680 | 9/1999 |

\* cited by examiner

*Primary Examiner*—Glenn Caldarola
*Assistant Examiner*—Alexis Wachtel
(74) *Attorney, Agent, or Firm*—Eric T. Addington; Dare M. Kendell; Ken K. Patel

(57) ABSTRACT

The present invention is directed to an elastic laminate which is elastically extensible in at least one direction. The elastic laminate includes an elastomeric material having a first surface and a second surface opposing the first surface; and a first nonwoven layer joined to the first surface of the elastomeric material. The first nonwoven layer is formed from component fibers having a primary fiber direction. The first nonwoven layer has a Fiber Orientation Ratio within about ±20 degrees from a primary fiber direction of at least about 65%. The present invention is also directed to a disposable garment employing such an elastic laminate.

19 Claims, 11 Drawing Sheets

ELASTIC LAMINATE INCLUDING NONWOVEN LAYER FORMED FROM HIGHLY-ORIENTED-COMPONENT FIBERS AND DISPOSABLE GARMENT EMPLOYING THE SAME

FIELD

The present invention relates to elastic laminates. More specifically, the present invention relates to elastic laminates which includes a nonwoven layer formed from highly oriented component fibers. The present invention also relates to disposable garments employing such elastic laminates. Examples of such disposable garments include disposable underwear, disposable diapers including pull-on diapers and training pants, and disposable panties for menstrual use.

BACKGROUND

Elastic laminates have previously been used in a variety of disposable products, including sweat bands, bandages, body wraps, and disposable garments including disposable diapers and incontinence devices. Herein, "elastic laminate" refers to an elastically stretchable two or more layered materials including at least one elastically stretchable single layer material. It is generally expected that these products provide good fit to the body and/or skin of the user by using suitable elastic members during the entire use period of products.

A "zero strain" stretch laminate is one type of elastic laminate which is preferably used for such disposable products. For example, methods for making "zero strain" stretch laminate webs are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992. In a manufacturing process for such "zero strain" stretch laminate, the elastomeric material is operatively joined to at least one component material in a substantially untensioned (zero strain) condition. At least a portion of the resultant composite stretch laminate is then subjected to mechanical stretching sufficient to permanently elongate the non-elastic components. The composite stretch laminate is then allowed to return to its substantially untensioned condition. Thus, the elastic laminate is formed into a "zero strain" stretch laminate. Herein, "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching.

As is noted in the above, the manufacturing process of such "zero strain" stretch laminate includes the step of subjecting the non-elastic composite stretch laminate to mechanical stretching sufficient to permanently elongate the non-elastic components. This step is additional to normal elastic lamination processes and gives limitations to materials to be used in the elastic laminate. For example, the elastomeric material and other composite material(s) used in the elastic laminate need to have enough physical strength or toughness since those materials tend to be mechanically damaged by the process. If the elastomeric material, for example, does not have enough strength or toughness, the elastomeric material tends to be easily shred or torn by the stress which is applied to the elastomeric material during the mechanical stretching in the manufacturing process and during the use of products.

Based on the foregoing, there is a need for an elastic laminate that does not have such limitations to the elastomeric material to be used therein.

Infants and other incontinent individuals wear disposable garments such as diapers to receive and contain urine and other body exudates. One type of the disposable garments, which is often called as "tape type", has a fastener system to hold the disposable garment at the wearer's waist area. As the fastener system, either an adhesive tape system or a mechanical fastener system is often used. Recently, elastically stretchable ear panels tend to be preferably used in this type of disposable garment, because they can provide a better fit to the wearer's waist area by jointly working with the fastener system. Another type of disposable garments, which is often called as "pant type" or "pull-on", has fixed sides and has become popular for use on children able to walk and often who are toilet training. This type of pull-on garments has ear panels the edges of which are seamed together to form two leg openings and a waist opening. They also has a stretchable waistband disposed along at least one of the end edges of the disposable garments. These pull-on garments need to fit snugly about the waist and legs of the wearer without drooping, sagging or sliding down from position on the torso to contain body exudates. Examples of these pull-on garments are disclosed, for example, in U.S. Pat. No. 5,171,239 to Igaue et al., U.S. Pat. No. 4,610,681 to Strohbeen et al., WO 93/17648 published on Sep. 16, 1993, U.S. Pat. No. 4,940,464 to Van Gompel et al., U.S. Pat. No. 5,246,433 to Hasse et al., and U.S. Pat. No. 5,569,234 to Buell et al.

Good performance characteristics of such stretchable ear panels and waistband are important for these types of disposable garments. More specifically, the extension properties including the extension forces, recovery forces, retention forces, and available stretch (extension) of the ear panels and waistband are important considerations in the performance of the fitness for pull-on garments. The extension properties provide the applicator and the wearer with the overall perceived "stretchiness" during use. They also effect the ability of the applicator to achieve a suitable degree of application stretch (i.e., for a "normally" perceived tensioning of the diaper during application, the total amount of resultant stretch is that desired to achieve/maintain good conformity of fit).

To provide good performance characteristics in stretchable ear panels and waistband of disposable garments, elastic laminates which include an elastic material which has suitable properties have been studied and applied to disposable garments. For example, a PCT application No. PCT/US98/05895 entitled "Elastic Member And Disposable Garment Having Improved Fitness To Body During Entire Use" filed on Mar. 26, 1998, discloses such elastic materials for disposable garments. It is generally expected that disposable garments provide good fit to the body and/or skin of the user by using suitable elastic laminates during the entire use period of products. Typical examples of such elastic laminates that have been previously used include composites formed from an elastic material joined to a non(or less)-elastic material such as nonwoven fabrics and plastic films. These non(or less)-elastic materials tend to affect expected elastic properties of elastic laminates. For example, those materials tend to decrease elastic "stretchiness" of the stretchable ear panels during use.

Based on the foregoing, there is also a need for disposable garments which employ an elastic laminate that does not decrease elastic "stretchiness" thereof.

SUMMARY

The present invention is directed to an elastic laminate which is elastically extensible in at least one direction. The elastic laminate includes an elastomeric material having a first surface and a second surface opposing the first surface; and a first nonwoven layer joined to the first surface of the elastomeric material. The first nonwoven layer is formed from component fibers having a primary fiber direction. The first nonwoven layer has a Fiber Orientation Ratio within about ±20 degrees from the primary fiber direction of at least about 65%.

The present invention is also directed to a disposable garment having a front region, a back region and a crotch region between the front region and the back region. The disposable garment comprises a chassis provided in the front, back and crotch regions and having edge lines in the front and back regions. The chassis includes a liquid pervious topsheet, a liquid impervious backsheet associated with the topsheet, and an absorbent core disposed between the topsheet and the backsheet.

In one aspect of the present invention, the disposable garment further comprises at least one pair of extensible side panels extending laterally outward from the chassis in the front or back region. At least one of the side panels includes an elastic laminate elastically extensible at least in the lateral direction. The elastic laminate includes an elastomeric material having a first surface and a second surface opposing the first surface; and a first nonwoven layer joined to the first surface of the elastomeric material. The first nonwoven layer is formed from component fibers having a primary fiber direction. The first nonwoven layer has a Fiber Orientation Ratio within about ±20 degrees from a primary fiber direction of at least about 65%.

In another aspect of the present invention, the disposable garment further comprises a waistband disposed along at least one of the end edges of the disposable garment. The waistband includes an elastic laminate elastically extensible at least in the lateral direction. The elastic laminate includes an elastomeric material having a first surface and a second surface opposing the first surface; and a first nonwoven layer joined to the first surface of the elastomeric material. The first nonwoven layer is formed from component fibers having a primary fiber direction. The first nonwoven layer has a Fiber Orientation Ratio within about ±20 degrees from a primary fiber direction of at least about 65%.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

DETAILED DESCRIPTION

All cited references are incorporated herein by reference in their entireties. Citation of any reference is not an admission regarding any determination as to its availability as prior art to the claimed invention.

Herein, "comprise", "include" and "have" mean that other element(s) and step(s) which do not affect the end result can be added. These terms encompass the terms "consisting of" and "consisting essentially of".

Herein, "gf" stands for gram force.

Herein, "joined" or "joining" encompasses configurations whereby an element is directly secured to another by affixing the element directly to the other element, and configurations whereby the element is indirectly secured to the other element by affixing the element to intermediate member(s) which in turn are affixed to the other element.

Herein, "layer" does not necessarily limit the element to a single stratum of material in that a layer may actually comprise laminates or combinations of sheets or webs of materials.

Herein, "nonwoven" may include any material which has been formed without the use of textile weaving processes which produce a structure of individual fibers which are interwoven in an identifiable manner. Methods of making suitable nonwovens includes a spunbonded nonwoven process, a meltblown nonwoven process, a carded nonwoven process, or the like.

A. Laminate Structure

The present invention relates to an elastic laminate which does not have a limitation(s) to an elastomeric material to be used therein. This and other advantages of the invention are described in more detail herein.

Figure 1:
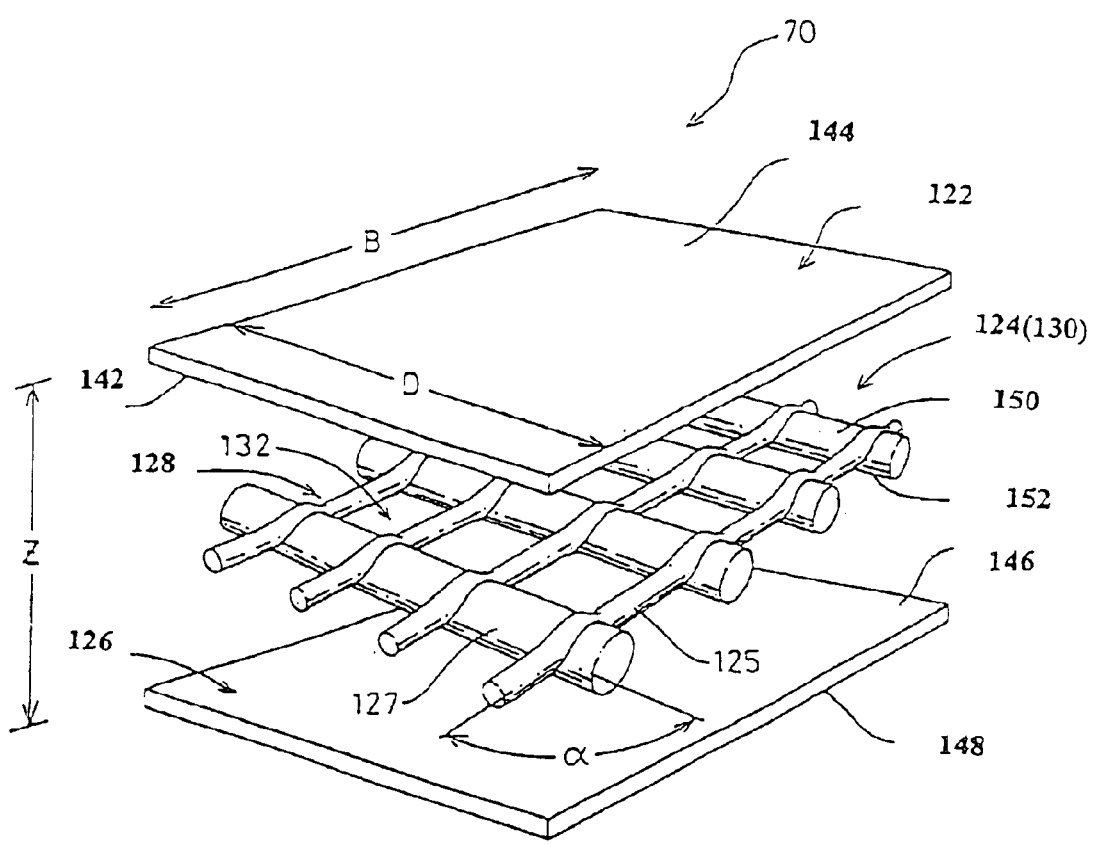
FIG. 1 is a fragmentary enlarged perspective view of an elastic laminate of one preferred embodiment of the present invention, prior to being formed into the elastic laminate.
Figure 2:
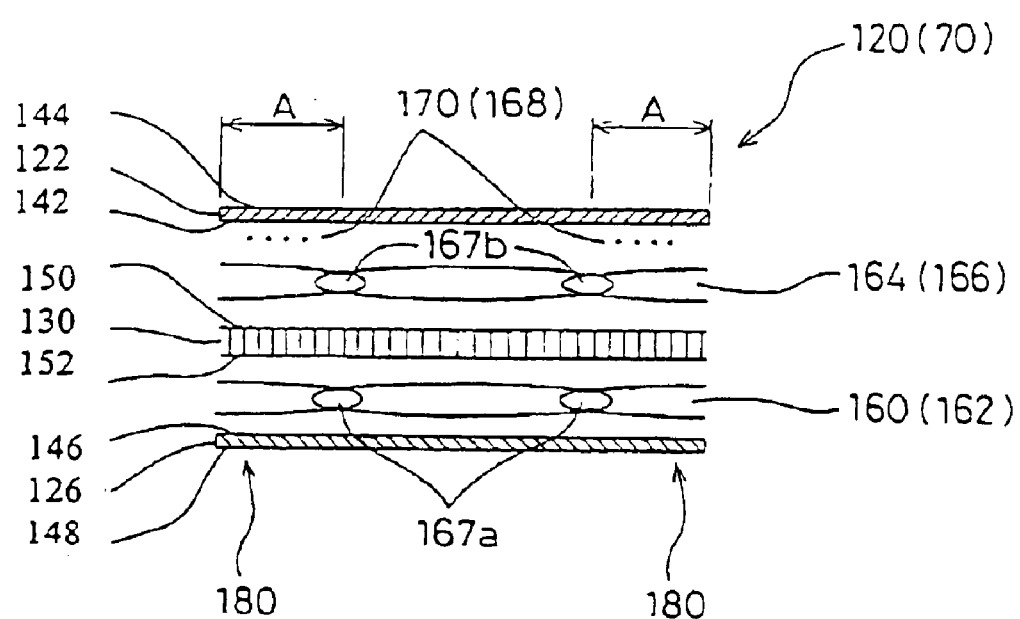
FIG. 2 is a simplified cross-sectional view of an elastic laminate of another preferred embodiment.
Figure 3:
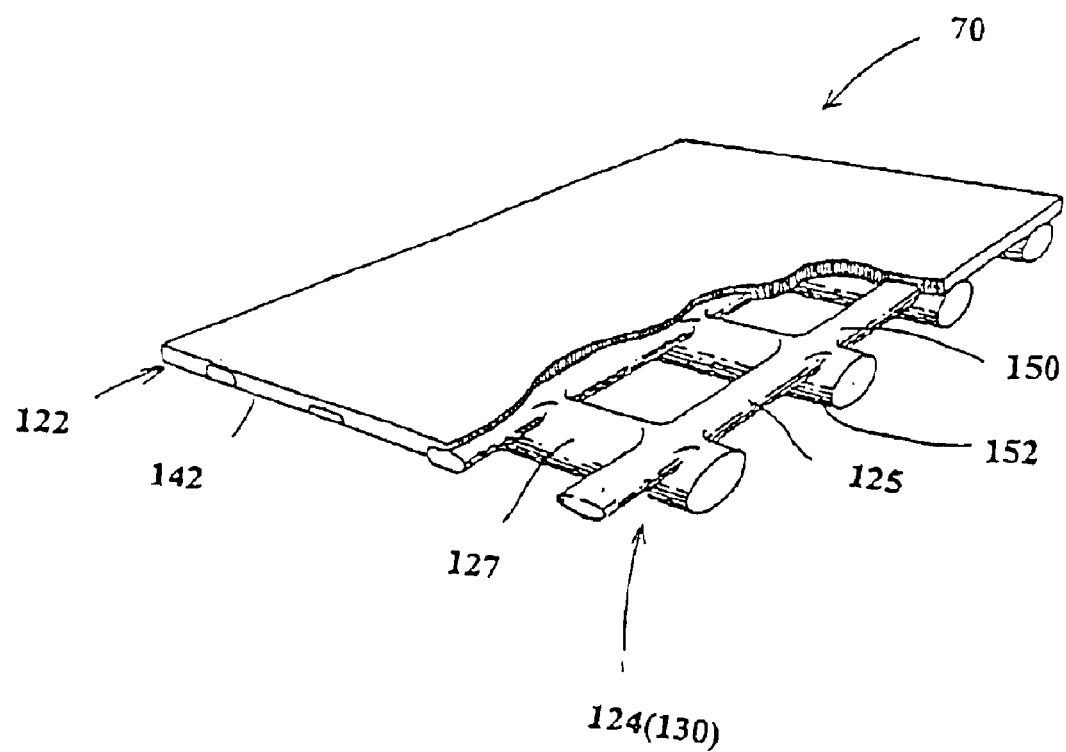
FIG. 3 is a enlarged perspective view of an elastic laminate of yet another embodiment of the present invention, wherein a portion of the nonwoven layer has been removed to show the bonded structure.

FIG. 1 is a fragmentary enlarged perspective view of an elastic laminate 70 of one preferred embodiment, prior to being formed into the elastic laminate. (Preferred embodiments of the elastic laminate 70 after the formation are shown in FIGS. 2 and 3.) Referring to FIG. 1, the elastic laminate 70 of the present invention includes an elastomeric layer 124 having a first surface 150 and a second surface 152 opposing the first surface 150; and a first nonwoven layer 122 which is joined to the first surface 150 of the elastomeric layer 124. In a preferred embodiment, the first surface 150 and second surface 152 of the elastomeric layer 124 are substantially parallel with the plane of the first nonwoven layer 122. The first nonwoven layer 122 has an inner surface (or a first surface) 142 and an outer surface (or a second surface) 144. The inner surface 142 of the first nonwoven layer 122 is the surface that is positioned facing the elastomeric layer 124.

In a preferred embodiment, the elastic laminate 70 further comprises a second nonwoven layer 126 joined to the second surface 152 of the elastic material 70. The second nonwoven layer 126 also has an inner surface 146 and an outer surface 148. The inner surface 146 of the second nonwoven layer 126 is the surface that is positioned facing the elastomeric layer 124. The second surface 152 of the elastomeric layer 124 is substantially parallel with the plane of the second nonwoven layer 126. In a preferred embodiment, the nonwoven layer 126 is formed by an identical nonwoven material with that is employed in the first nonwoven layer 122. Alternatively, the nonwoven layer 126 may be formed by a different material from that is employed in the first nonwoven layer 122.

The elastic laminate 70 of the present invention is elastically extensible in at least one direction (first direction). For example, the elastic laminate 70 shown in FIG. 1 is elastically extensible in the structural direction D. Herein, "structural direction" (e.g., D and B) is intended to mean a direction which extends substantially along and parallel to the plane of the first nonwoven layer 122. In a preferred embodiment, the elastic laminate 70 is also elastically extensible in the second direction which is perpendicular to the first direction. For example, the elastic laminate 70 shown in FIG. 1 is also elastically extensible in the structural direction B.

B. Nonwoven Layers

The first nonwoven layer 122 of the present invention is formed from component fibers which are joined together. The component fibers have a primary fiber direction. The first nonwoven layer 122 has a Fiber Orientation Ratio within about +20 degrees from the primary fiber direction (FOR20) of at least about 65%; more orefarably at least about 75%; more preferably still at least about 85%. In a more preferred embodiment, the first nonwoven layer 122 additionally has a Fiber Orientation Ratio within about ±10 degrees from the primary fiber direction (FOR10) of at least about 45%; more preferably at least about 60%; more preferably still at least about 70%.

"FOR#" (e.g., FOR10) indicates the ratio of the number of the component fibers whose directions are within about ±# degrees, (e.g., ±10 degrees) from the primary fiber direction to the total number of component fibers. Herein, "primary fiber direction" refers to an average direction of component fibers in the nonwoven layer. One preferred method for measuring the Fiber Orientation Ratio of nonwoven layers is explained in more detail below.

In a preferred embodiment, the first nonwoven layer 122 has a Tensile Strength Ratio (TSR) of at least about 15, more preferably at least about 60. The TSR is defined by the following calculation:

$$TSR = TS1/TS2 \qquad (1)$$

wherein,

TS1 (gf/inch): a tensile strength (TS) at the breaking point in the primary fiber direction; and TS2 (gf/inch): a tensile strength (TS) at the breaking point in the perpendicular direction which is perpendicular to the primary fiber direction.

Tensile Strength (ST) is measured as the maximum tensile strength value recorded while the first nonwoven layer 122 is stretched at a rate of about 20 inches/min (about 50 cm/min) to its breaking point. The tensile strength of the first nonwoven layer 122 is measured before the first nonwoven layer 122 is joined to the elastomeric layer 124.

In a preferred embodiment, the first nonwoven layer 122 has a tensile strength of less than about 200 gf/inch (about 80 gf/cm) at 30% elongation to the direction which is perpendicular to the primary fiber direction; more preferably less than about 100 gf/inch (about 40 gf/cm), more preferably still less than about 50 gf/inch (about 20 gf/cm).

The first nonwoven layer 122 may be manufactured from a wide range of component fibers including, e.g., natural fibers (e.g., wool and cotton fibers), synthetic fibers (e.g., polyolefin, polyester, nylon, and rayon fibers), or a mixture of natural fibers and/or synthetic fibers. For ease of manufacture and cost efficiency, the first nonwoven layer 122 is preferably formed from synthetic continuous fibers. More preferably, such synthetic continuous fibers are formed from a polyolefin (e.g., polyethylene and polypropylene) or a polyester. Preferred polyester material includes a polyethylene terephthalate, a polybutylene terephthalate and a polypropylene terephthalate, or mixtures thereof. In a preferred embodiment, the first nonwoven layer 122 additionally includes component fibers formed from the other materials (i.e., non-polyester materials) such as polyolefin and nylon.

In a preferred embodiment, the individual component fibers are formed from a single type of material which is selected from the above materials (i.e. the individual fiber is not made from polyolefin and nylon). Preferably, the component fibers are formed from a polyester, more preferably a polyethylene terephthalate, or one of its relatives which has an average molecular weight from about 5,000 to about 60,000, preferably from about 10,000 to about 40,000, more preferably from about 14,000 to about 23,000. Alternatively, the component fibers may be formed from a mixture of two (or more) materials which are selected from the above materials.

In one embodiment, the component fiber has a bi-component fiber structure formed from two distinct materials of a polyester and a polyolefin. In an alternative embodiment, the component fiber has a bi-component fiber structure formed from two distinct molecular weight materials of one identical material, for example, a polyester. Preferred bi-component fiber structures may include a side-by-side bi-component fiber structure and a sheath-core bi-component fiber structure known in the art. In one embodiment, the component fiber has a bi-component fiber structure having a core of polyolefin and a sheath of a polyester.

In a preferred embodiment, the first nonwoven layer 122 has a basis weight of less than about 60 g/m², and comprises fibers having a fiber diameter of less than about 50 μm. More preferably, for products such as disposable garment and the like, the first nonwoven layer 122 has a basis weight of from about 3 g/m$^2$ to about 50 g/m$^2$, more preferably from about 10 g/m$^2$ to about 25 g/m$^2$, and a fiber diameter of from about 1 μm to about 30 μm, more preferably from about 3 μm to about 20 μm.

The component fibers may be joined together by adhesives, thermal bonding, water-jetting, needling/felting, or other methods known in the art to form nonwoven fabrics. In a preferred embodiment, the first nonwoven layer 122 is formed from a nonwoven manufacturing process handling continuous component fibers or filaments known in the art. Preferred manufacturing process are described in, for example, EP 0843036A1 (Kurihara et al.) published on May 20, 1998; U.S. Pat. No. 5,312,500, entitled "Non-Woven Fabric and Method and Apparatus for Making The Same", issued to Kurihara et al. on May 17, 1994; Japanese Laid-Open Patent Publication (Kokai) No. H2-269859 published on Nov. 5, 1990; and Japanese Patent Publication (Kokoku) No. S60-25541 published on Jun. 19, 1985.

Preferred nonwoven fabrics which are suitably applicable to the first nonwoven layer 122 are available from Nippon Petrochemicals Co., Ltd., Tokyo, Japan, under Code Nos. MBE8202-3-2; MBE8202-3-1; MBE7711-2; MBE6515-10; and MBE7922-1 which have the following properties.

TABLE

| Code No. | Basis Weight (g/m$^2$) | FOR10 (%) | FOR20 (%) | TSR at Break Point | TS at 30% elongation |
|---|---|---|---|---|---|
| MBE8202-3-2 | 15 | 77 | 93 | 106 | 10 |
| MBE8202-3-1 | 20 | 82 | 94 | 68 | 20 |
| MBE7711-2 | 21 | 69 | 92 | 76 | 133 |
| MBE6515-10 | 8 | 60 | 85 | 104 | 21 |
| MBE7922-1 | 29 | 58 | 80 | 33 | 157 |

C. Elastomeric Material

The elastomeric layer 124 may be formed in a wide variety of sizes, forms and shapes. In a preferred embodiment, the elastomeric layer 124 is in the form of a continuous plane layer such as shown in, for example, FIG. 1. Preferred forms of a continuous plane layer include a scrim, a perforated (or apertures formed) film, an elastomeric woven or nonwoven, and the like. Preferably, the elastomeric layer 124 has a thickness of from about 0.05 mm to about 1 mm (about 0.002 inch–about 0.039 inch). The continuous plane layer may take any shape which can be suitably provided in products. Preferred shapes of a continuous plane layer include a quadrilateral including a rectangle and a square, a trapezoid, and the other polygons. In an alternative embodiment, the elastomeric layer 124 is in the form of discrete strands (or strings) which are not connected each other.

The elastomeric material of the present invention may include all suitable elastic materials known in the art. Elastomeric materials suitable for use herein include synthetic or natural rubber materials known in the art. Preferred elastomeric materials include the diblock and triblock copolymers based on polystyrene and unsaturated or fully hydrogenerated rubber bolcks, and their blends with other polymers such as polyolefin polymers.

In a preferred embodiment, the elastomeric material is made from a polystyrene thermoplastic elastomer including styrene block copolymer based materials. A preferred styrenic block copolymer based material contains from about 1 wt % to about 70 wt % of polystyrene, more preferably from about 10 wt % to about 50 wt % of polystyrene.

Preferably, the polystyrene thermoplastic elastomer is selected from the group consisting of a styrene-butadiene-styrene thermoplastic elastomer, a styrene-isopren-styrene thermoplastic elastomer, a styrene-ethylene/butylene-styrene thermoplastic elastomer, a styrene-ethylene/propylene-styrene thermoplastic elastomer, a styrene-ethylene/propylene thermoplastic elastomer, a hydrogenated styrene butadiene rubber, and a mixture thereof.

A preferred styrenic block copolymer based material contains from about 1 wt % to about 70 wt % of polystyrene, more preferably from about 10 wt % to about 50 wt % of polystyrene.

Figure 4:
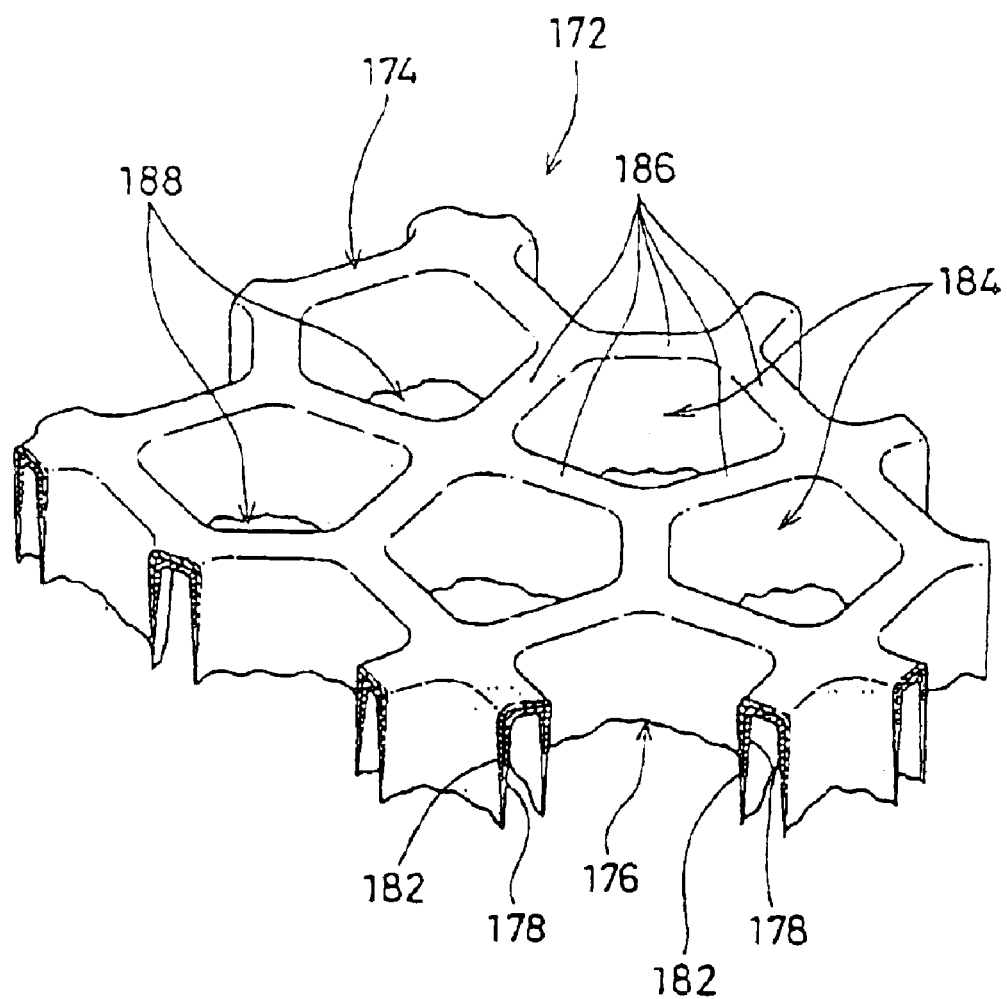
FIG. 4 is a fragmentary enlarged perspective view of an alternative embodiment of the elastomeric material.

In an alternative preferred embodiment, the elastomeric material 124 is a porous, macroscopically-expanded, three-dimensional elastomeric web 172 as shown in FIG. 4. The web 172 has a continuous first surface 174 and a discontinuous second surface 176 opposing to the first surface 174. The elastomeric web 172 preferably comprises a formed film interconnecting member 186 including at least two polymeric layers 178 and 182. The first layer 178 is substantially elastic and the second layer 182 is substantially less elastic than the first layer 178. At least one of the two polymeric layers 178 and 182 is formed from a polystyrene thermoplastic elastomer. The elastomeric web 172 exhibits a multiplicity of primary apertures 184 in the first surface 174 of the web 172. The primary apertures 184 are defined in the plane of the first surface 174 by a continuous network of the interconnecting member 186. The interconnecting member 186 exhibits an upwardly concave-shaped cross-section along its length. The interconnecting member 186 also forms secondary apertures 188 in the plane of the second surface 176 of the web 172. The apertures 184 and 188 may take any shape. A preferred elastomeric web is disclosed in U.S. patent application Ser. No. 08/816,106, filed on Mar. 14, 1997. A preferred porous elastomeric material for the elastomeric layer 124 is available from Tredegar Film Products under the designation X-25007.

In one preferred embodiment, the elastomeric layer 124 is in the form of a scrim 130 as shown in FIG. 1. The elastomeric scrim 130 comprises a plurality of first strands 125 which intersect or cross (with or without bonding to) a plurality of second strands 127 at nodes 128 at a predetermined angle α, thereby forming a net-like open structure having a plurality of apertures 132. Each aperture 132 is defined by at least two adjacent first strands 125 and at least two adjacent second strands 127 such that apertures 132 are substantially rectangular (preferably square) in shape. Other aperture configurations, such as parallelograms or circular arc segments, can also be provided. Such configurations could be useful for providing non-linear elastic structural directions. Preferably, the first strands 125 are substantially straight and substantially parallel to one another; and, more preferably, the second strands 127 are also substantially straight and substantially parallel to one another. More preferably, first strands 125 intersect second strands 127 at nodes 128 at a predetermined angle a of about 90 degrees. Each node 128 is an overlaid node, wherein first strands 125 and second strands 127 are preferably joined or bonded (although it is contemplated that joining or bonding may not be required) at the point of intersection with the strands still individually distinguishable at the nodes 128. However, it is believed that other node configurations such as merged or a combination of merged and overlaid would be equally suitable.

Although it is preferred that first and second strands 125 and 127 be substantially straight, parallel, and intersect at an angle a of about 90 degrees, it is noted that first and second strands 125 and 127 can intersect at other angles α, and that first strands 125 and/or second strands 127 can be aligned in circular, elliptical or otherwise nonlinear patterns relative to one another. Although for ease of manufacture it is contemplated that first strands 125 and second strands 127 have a substantially circular cross-sectional shape prior to incorporation into elastic laminate 70 (as shown in FIG. 1), the first and second strands 125 and 127 can also have other cross-sectional shapes such as elliptical, square, triangular or combinations thereof.

Preferably, the material for the first strands 125 is chosen so that the first strands 125 can maintain the second strands 127 in relative alignment prior to forming elastic laminate 70. It is also desirable that the materials for the first and second strands 125 and 127 are capable of being deformed (or initially formed) into predetermined shapes upon application of a predetermined pressure or a pressure in combination with a heat flux prior to forming elastic laminate 70. These deformed shapes (e.g., elliptical second strands, substantially flat first strands and the like) can provide an elastic laminate 70 which can be comfortably worn about the body without irritation or other discomfort.

In a preferred embodiment, the first and second strands 125 and 127 are formed from an identical elastomeric material. For example, the first and second strands 125 and 127 are formed from an identical polystyrene thermoplastic elastomer which is selected from the group consisting of a styrene-butadiene-styrene thermoplastic elastomer, a styrene-isopren-styrene thermoplastic elastomer, a styrene-ethylene/butylene-styrene thermoplastic elastomer, a styrene-ethylene/propylene-styrene thermoplastic elastomer, a styrene-ethylene/propylene thermoplastic elastomer, a hydrogenated styrene butadiene rubber or an unsaturated styrene butadiene rubber, and a mixture thereof. A preferred elastomeric scrim 124 which containes a styrene-butadiene-styrene thermoplastic elastomer is manufactured by the Conwed Plastics Company (Minneapolis, Minn., U.S.A.) under the designation X02514. This material has about 12 elastic strands per inch (about 5 strands/cm) in the structural direction B (i.e., the first strands 125) and about 7 elastic strands per inch (about 3 strands/cm) in the structural direction D (i.e., the second strands 127) before lamination.

Alternatively, the first and second strands 125 and 127 are formed from two different material. For example, one of the first and second strands 125 and 127 is formed from one of the above described polystyrene thermoplastic elastomer, while the other of the first and second strands 125 and 127 is formed from material(s) other than the above described polystyrene thermoplastic elastomer. Such other material(s) may be either elastic or non-elastic, and selected from suitable materials known in the art.

D. Joining Nonwoven to Elastomeric Material

The first nonwoven layer 122 of the present invention can be joined to the elastomeric layer 124 by any means known in the art. In a preferred embodiment, the first nonwoven layer 122 is joined to the first surface 150 of the elastomeric layer 124 by an adhesive means such as those well known in the art. For example, the first nonwoven layer 122 may be secured to the first surface 150 of the elastomeric layer 124 by a uniform continuous layer of adhesive, a patterned layer of adhesive, or an array of separate lines or spots of adhesive. One preferred laminate structure formed by an adhesive means is shown in FIG. 2.

FIG. 2 shows a simplified fragmentary enlarged side view looking into the structural direction B of the elastic laminate 70. In this embodiment, the elastic laminate 70 includes the second nonwoven layer 126. Referring to FIG. 2, a first adhesive 170 is applied to the inner surface 142 of the first nonwoven layer 122 in positions that correspond to each of the outer edges 180 of the laminate structure 120. The first adhesive 170 may alternatively or additionally be applied to the inner surface 146 of the second nonwoven layer 126. For ease of illustration, the description and Figs. refer to application to the first nonwoven layer 122 only.

This pattern creates side anchor zones A, which substantially eliminate the delamination and creep associated with previously known laminates and which allows the elastic laminate 70 to experience higher strains without creeping or delaminating. It has also been found that confining the first adhesive 170 to the edge areas 180 of the laminate structure 120 avoids impeding the extensibility of the elastic laminate 70 and also avoids tears in the nonwoven layers 122 and 126. Preferably, the first adhesive 170 is applied as a plurality of beads 168, as shown in FIG. 2. Preferably, the first adhesive 170 is a flexible adhesive with an amorphous and crystallizing component. Such a preferred adhesive is made by Ato Findley Inc., WI, U.S.A., under the designation H9224.

The side anchoring is preferably performed by side gluing with adhesive beads to anchor the elastomeric layer 124 between the nonwoven layers 122 and 126 as a part of the lamination process. Alternatively, side anchoring may be performed by sewing, heat sealing, ultrasonic bonding, needle punching, alternative gluing processes, or by any other means known to those skilled in the art.

More preferably, the elastic laminate 70 includes a second adhesive 164. Preferably, the second adhesive 164 is an elastomeric adhesive. The second adhesive 164 is preferably applied to the first surface 150 of the elastomeric layer 130. The second adhesive 164 is preferably applied in a spiral spray pattern 166, thereby forming bond points 167*b* that are more discrete than would be formed by a linear spray application. Without being bound by theory, it is believed that most of the second adhesive 164 is sprayed in the structural direction D (FIG. 1). Preferably, the layer of second adhesive 164 is directly applied onto the first surface 150 of the elastomeric layer 124 in the lamination process.

A third adhesive 160 may also preferably be applied to the inner surface 146 of the second nonwoven layer 126. Preferably, the third adhesive 160 is an elastomeric adhesive. In a manner similar to that described with reference to the second spiral adhesive application 166, the third adhesive 160 is preferably applied in a spiral spray pattern 162, thereby forming bond points 167*a* that are more discrete than would be formed by a linear spray application. Preferably, the layer of third adhesive 160 is directly applied onto the second surface 152 of the elastomeric layer 124 in the lamination process.

Preferably, second and third adhesives 160 and 164 are the same elastomeric adhesive. A preferred adhesive for use in the second and third adhesive spiral sprays 162 and 166 is made by Ato Findley Inc., WI, U.S.A., under the designation H2120. Preferably, the add-on level for each of the second and third spiral sprays 162 and 166 is about 4 mg/inch (about 1.6 mg/cm) to about 12 mg/inch (about 4.8 mg/cm), more preferably about 8 mg/inch (about 3.2 mg/cm).

In an alternative preferred embodiment, the first nonwoven layer 122 is bonded to the first surface 150 of the elastomeric layer 124 by forming a heat/pressure bond between the first nonwoven layer 122 and the elastomeric layer 124. Herein, "heat/pressure bond" is either a physical or chemical bond formed by an application of appropriate heat and pressure to two different members so that the two members can have a portion which has an increased peel strength by the formation of the bond. Herein, "peel strength" refers to the amount of force required to separate the two members from each other. Higher peel strengths typically equate to less chance of de-lamination of the elastic laminates in use of products. To form such heat/pressure bond(s) between the first nonwoven layer 122 and the elastomeric layer 124, any pressure can be applied to the first nonwoven layer 122 and the elastomeric layer 124 at a certain temperature as long as it does not substantially damage the physical and/or chemical properties of the resulting elastic laminate.

FIG. 3 is a partial perspective view of an elastic laminate 70 of yet another embodiment, wherein a portion of the first nonwoven layer 122 has been removed to show the heat/pressure bond structure. In FIG. 3, the elastomeric scrim 130 which is formed by the first and second strands 125 and 127 is used as an example for the elastomeric layer 124. Referring to FIG. 3, the first nonwoven layer 122 is bonded to the first surface 150 of the elastomeric layer 124 by forming a heat/pressure bond between the first nonwoven layer 122 and the elastomeric layer 124. In a preferred embodiment, the elastic laminate further includes a second nonwoven layer (not shown in FIG. 3) which is bonded to the second surface 152 of the elastomeric layer 124 by forming another heat/pressure bond therebetween.

The heat/pressure bond is formed by softening only the material of the elastomeric layer 124 (i.e., without melting the component fibers of the first nonwoven layer 122). This heat/pressure bond is preferably formed by application of a bonding temperature which is lower than the melting point of the material of the first nonwoven layer 122. This generally results in a decrease in the viscosity of the material which may or may not involve a "melting" of the material. As a result, the component materials of the elastomeric layer 124 are softened to form the heat/pressure bond. In a more preferred embodiment wherein the elastomeric layer 124 is formed from a polystyrene thermoplastic elastomer including a polystyrene segment, a bonding temperature which is higher than the glass transition temperature of the polystyrene segment is applied for forming the heat/pressure bond.

Figure 5:
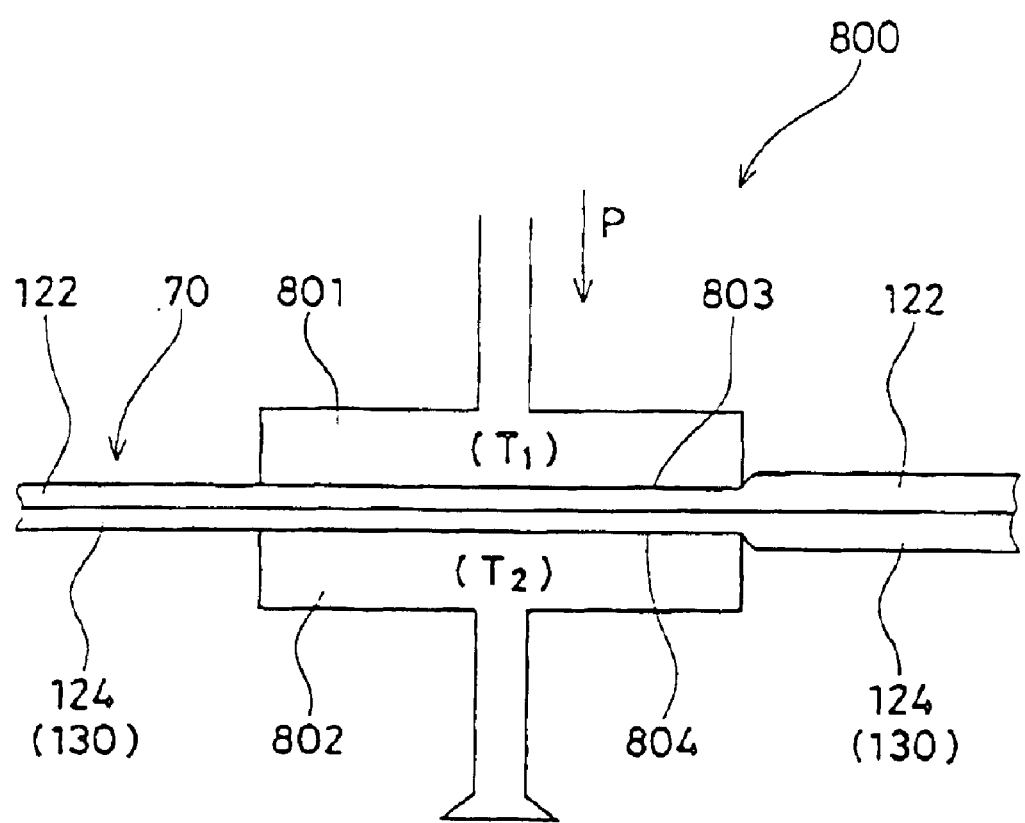
FIG. 5 is a schematic representation of a lamination device for forming the elastic laminate shown in FIG. 3.

FIG. 5 shows one preferred example of a lamination device for forming the elastic laminate 70 shown in FIG. 3. Referring to FIG. 5, the lamination device 800 includes a first pressure plate 801 having a first surface 803, and a second plate 802 having a second surface 804. The second pressure plate 802 is fixed, while the first pressure plate 801 is movable to apply a pressure P to the first nonwoven layer 122 and the elastomeric layer 124 in cooperation with the second pressure plate 802. Preferably, the first and second surfaces 803 and 804 are substantially plane and are substantially parallel each other. The first nonwoven layer 122 is juxtaposed with the elastomeric layer 124 such that the first nonwoven layer 122 is immediately adjacent the elastomeric layer 124. The juxtaposed two layers 122 and 124 are manually supplied to the lamination device 800. A preferred lamination device 800 is available from Toyo Tester Industry Co., Ltd., Osaka, Japan, under a trade name "Heat Sealer".

In the lamination process, the first surface 803 is heated to a temperature T1, while the second surface 804 is heated to a temperature T2. Preferably, the temperature T1 is from about 80° C. to about 160° C., more preferably from about 100° C. to about 130° C. The temperature T2 is preferably from about 30° C. to about 60° C., more preferably from about 45° C. to about 55° C. The pressure P is preferably from about 6 kg/cm$^2$ to about 15 kg/cm$^2$, more preferably from about 9 kg/cm$^2$ to about 11 kg/cm$^2$. The time period of the application of the pressure P is preferably from about 1 second to about 20 seconds, more preferably from about 5 seconds to about 15 seconds. Preferably, the application of pressure P can be performed two (or more) times to increase the peel strength of the resulting laminate 70. By the application of the temperatures T1 and T2 at the pressure P, the elastomeric layer 124 is bonded to the first nonwoven layer 122 through a heat/pressure bond which is formed by softening the material of the elastomeric layer 124 (e.g., the polystyrene thermoplastic elastomer).

The elastic laminate 70 of the present invention can be incorporated into a variety of products wherein it is desired to provide an elastic stretchability in at least one structural direction either partially or entirely. Examples of such products include disposable products, including sweat bands, bandages, body wraps, and disposable garments including disposable diapers and incontinence products.

E. Test Methods

1. Test Method for Fiber Orientation

The following method is preferably used to determine the Fiber Orientation Ratio (FOR) of nonwoven material.

A sample nonwoven fabric (or layer) is placed on a specimen stub. The sample nonwoven fabric is fixed on the specimen stub at a flat condition so that the primary fiber direction (to be defined hereinafter) of the sample nonwoven fabric can be roughly aligned with the longitudinal direction of the photograph to be taken. A scanning electron microscope (SEM) is used to take a photograph at 50X magnification. A preferred SEM is available from Japan Electron Optics Laboratory (JEOL) Ltd., Tokyo, Japan, under Code No. JSM-5310.

The following analysis is conducted on the photograph by using a digitizer. A preferred digitizer is available from Graphtec Co., Ltd., Tokyo, Japan, under Code No. KD9600. A photograph is placed on the digitizer. A square area (500 $\mu$m×500 $\mu$m) is chosen at will in the photograph on the digitizer. The both ends of every component fiber which can be seen in the square area are manually identified by an operator and the coordinates thereof are detected and recorded by the digitizer. This work is conducted on three different square areas (each having 500 $\mu$m×500 $\mu$m) which are chosen at will in the photograph to obtain coordinate data on the all fibers in the three different square areas. The orientation angle of each fiber is calculated based on the coordinate data. The primary fiber direction of the sample nonwoven fabric is determined by the average orientation angle, which is an average value of the all orientation angle data obtained from the three different square areas.

The Fiber Orientation Ratio within about ±10 degrees (FOR10) is determined by the following calculation:

$$FOR10=NF10/TNF\times100 \qquad (2)$$

wherein,

NF10: the number of fibers which have orientation angles within about ±10 degrees from the primary fiber direction; and TNF: the total number of fibers measured within the three different square areas.

Similarly, the Fiber Orientation Ratio within about ±20 degrees (FOR20) is determined by the following calculation:

$$FOR20=NF20/TNF\times100 \qquad (3)$$

wherein,

NF20: the number of fibers which have orientation angles within about +20 degrees from the primary fiber direction.

2. Test Method for Tensile Strength

The following method is preferably used to measure the tensile strength of materials.

A tensile tester is prepared. The tensile tester has an upper jaw and a lower jaw which is located below the upper jaw. The upper jaw is movable and is connected to an extension force measuring means. The lower jaw is fixed in the tester. A test specimen (i.e., a nonwoven fabric to be measured) which has about 2.5 cm (about 1 inch) in width and about 10.2 cm (about 4 inches) in length is prepared and clamped with the upper jaw and the lower jaw so that the effective specimen length (L) (i.e., gauge length) is about 5.1 cm (about 2 inch). An extension force is continuously applied to the test specimen through the upper jaw at a cross-head speed of about 50 cm (about 20 inches) per minute, until the test specimen is physically broken. The applied extension force is recorded by a recorder (e.g., a computer system). The tensile strength at the breaking point is determined at the maximum tensile strength value. A tensile tester suitable for use is available from Instron Corporation (100 Royall Street, Canton, MA02021, U.S.A.) as Code No. Instron 5564.

F. Disposable Garments

Herein, "pull-on garment" refers to articles of wear which have a defined waist opening and a pair of leg openings and which are pulled onto the body of the wearer by inserting the legs into the leg openings and pulling the article up over the waist. Herein, "disposable" describes garments which are not intended to be laundered or otherwise restored or reused as a garment (i.e., they are intended to be discarded after a single use and, preferably, to be recycled, composted or otherwise disposed of in an environmentally compatible manner). A "unitary" pull-on garment refers to pull-on garments which are formed of separate parts united together to form a coordinated entity, but the ear panels are not separate elements joined to a separate chassis; rather, the ear panels are formed by at least one layer which also forms the chassis of the garment (i.e., the garment does not require separately manipulative panels such as a separate chassis and separate ear panels). The pull-on garment is also preferably "absorbent" to absorb and contain the various exudates discharged from the body. A preferred embodiment of the pull-on garment of the present invention is the unitary disposable absorbent pull-on garment, pull-on garment 120, shown in FIG. 6. Herein, "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. Herein, "panel" denotes an area or element of the pull-on garment. (While a panel is typically a distinct area or element, a panel may coincide (functionally correspond) somewhat with an adjacent panel.) Herein, "uncontracted state" is used herein to describe states of pull-on garments in its unseamed (i.e., seams are removed), flat and relaxed condition wherein all elastic materials used are removed therefrom.

Figure 6:
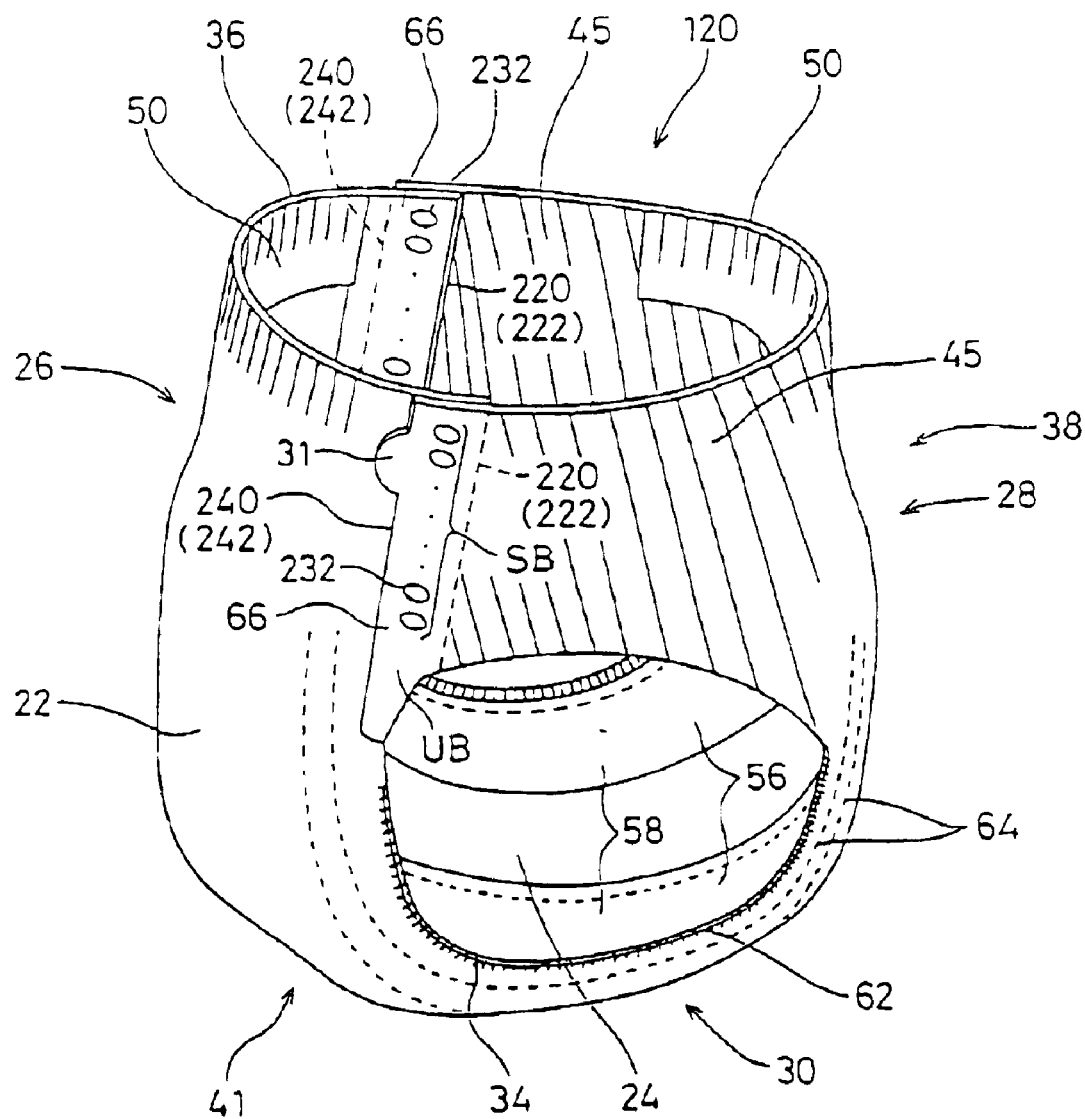
FIG. 6 is a perspective view of one preferred embodiment of the disposable pull-on garment of the present invention in a typical in use configuration.

FIG. 6 shows one preferred embodiment of a disposable pull-on garment of the present invention (i.e., a unitary disposable pull-on diaper 120). Referring to FIG. 6, the disposable pull-on garment 120 has a front region 26; a back region 28 and a crotch region 30 between the front region 26 and the back region 28. A chassis 41 is provided in the front, back and crotch regions 26, 28 and 30. The chassis 41 includes a liquid pervious topsheet 24, a liquid impervious backsheet 22 associated with the topsheet 24, and an absorbent core 25 (not shown in FIG. 6) disposed between the topsheet 24 and the backsheet 22. The chassis 41 has side edges 220 which form edge lines 222 in the front region 26.

The pull-on garment 120 further includes at least one pair of extensible ear panels 45 each extending laterally outward from the corresponding sides of the chassis 41. Each of the ear panels 45 has an outermost edge 240 which forms an outermost edge line 242. At least one of the outermost edge lines 242 has a nonuniform lateral distance from the longitudinal center line 100 (not shown in FIG. 6) in the uncontracted state of the garment 120.

In a preferred embodiment, the ear panels 45 continuously extend from the corresponding sides of the chassis 41 in the back region 28 to the corresponding side edges 220 of the chassis 41 in the front region 26 as shown in FIG. 6. Alternatively, the ear panels 45 may continuously extend from the corresponding sides of the chassis 41 in the front region 26 to the corresponding side edges of the chassis 41 in the back region 28 (not shown in FIG. 6).

The pull-on garment 120 has the ear panels 45 joined to the chassis 41 to form two leg openings 34 and a waist opening 36. Preferably, the pull-on garment 120 further includes seams 232 each joining the chassis 41 and the ear panels 45 along the corresponding edge lines 222 and 242 to form the two leg openings 34 and the waist opening 36.

Figure 7:
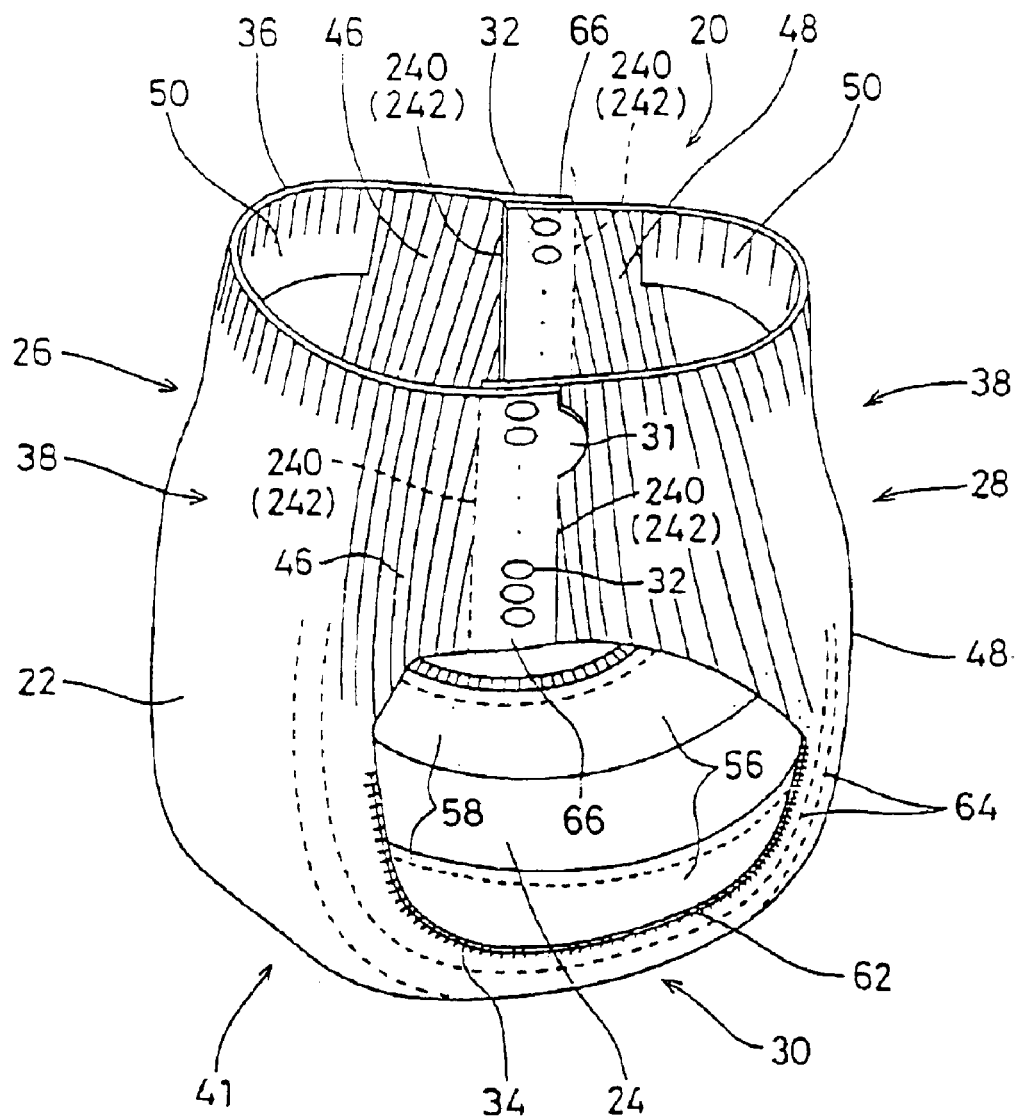
FIG. 7 is a perspective view of another preferred embodiment of the disposable pull-on garment of the present invention in a typical in use configuration.

FIG. 7 shows another preferred embodiment of a disposable pull-on garment of the present invention (i.e., a unitary disposable pull-on diaper 20). Referring to FIG. 7, the disposable pull-on garment 20 includes a pair of extensible front ear panels 46 each extending laterally outward from the corresponding sides of the chassis 41 in the front region 26, and a pair of extensible back ear panels 48 each extending laterally outward from the corresponding sides of the chassis 41 in the back region 28. Each of the ear panels 46 and 48 has an outermost edge 240 which forms an outermost edge line 242. At least one of the outermost edge lines 242 has a nonuniform lateral distance LD from the longitudinal center line 100 (not shown in FIG. 7 but in FIG. 8) in the uncontracted state of the garment 20. The pull-on garment 20 further includes seams 32 each joining the front and back ear panels 46 and 48 along the corresponding edge lines 242 to form the two leg openings 34 and the waist opening 36.

In a preferred embodiment, at least one of, more preferably both of, the pairs of the ear panels 45, 46 and 48 are elastically extensible in at least the lateral direction. In alternative embodiments, the ear panels 45, 46 and 48 are elastically extensible both in the lateral and longitudinal directions. Herein, "extensible" refers to materials that are capable of extending in at least one direction to a certain degree without undue rupture. Herein, "elasticity" and "elastically extensible" refer to extensible materials that have the ability to return to approximately their original dimensions after the force that extended the material is removed. Herein, any material or element described as "extensible" may also be elastically extensible unless otherwise provided. The extensible ear panels 45, 46 and 48 provide a more comfortable and contouring fit by initially conformably fitting the pull-on garment to the wearer and sustaining this fit throughout the time of wear well past when the pull-on garment has been loaded with exudates since the ear panels 45, 46 and/or 48 allow the sides of the pull-on garment to expand and contract.

The ear panels 45, 46 and 48 may be formed by unitary elements of the pull-on garment 20 or 120 (i.e., they are not separately manipulative elements secured to the pull-on garment 20 or 120, but rather are formed from and are extensions of one or more of the various layers of the pull-on garment). In a preferred embodiment, each of the ear panels 45, 46 and 48 is a projected member of the chassis 41 (more clearly shown in FIG. 8). Preferably, the ear panels 45, 46 and 48 include at least one unitary element or a continuous sheet material (e.g. the nonwoven outer cover 74 in FIG. 9) that forms a part of the chassis 41 and continuously extends into the ear panels 45, 46 and 48. Alternatively, the ear panels 45, 46 and 48 may be discrete members (not shown in Figs.) which do not have any unitary element that forms a part of the chassis 41, and may be formed by joining the discrete members to the corresponding sides of the chassis 41.

In a preferred embodiment, the pull-on garment 20 or 120 further includes seam panels 66 each extending laterally outward from each of the ear panels 45, 46 and 48; and tear open tabs 31 each extending laterally outward from the seam panel 66. In a preferred embodiment, each of the seam panels 66 is an extension of the corresponding ear panels 45, 46 and 48, or at least one of the component elements used therein, or any other combination of the elements. More preferably, each of the tear open tabs 31 is also an extension of the corresponding seam panel 66 or at least one of its component elements used therein, or any other combination of its elements.

In a preferred embodiment, the corresponding edge portions of the chassis 41 and/or the ear panels 45, 46 and 48 are seamed directly or indirectly (e.g., through the seam panels 66), in an overlaping manner to make an overlapped seam structure. Alternatively, the front and ear panels 46 and 48 can be seamed in a butt seam manner (not shown in Figs.). The bonding of the seams 32 can be performed by any suitable means known in the art appropriate for the specific materials employed in the chassis 41 and/or the ear panels 45, 46 and 48. Thus, sonic sealing, heat sealing, pressure bonding, adhesive or cohesive bonding, sewing, autogeneous bonding, and the like may be appropriate techniques. Preferably, the seam panels 66 are joined by a predetermined pattern of heat/pressure or ultrasonic welds which withstands the forces and stresses generated on the garment 20 or 120 during wear.

A continuous belt 38 is formed by the ear panels 45, 46 and 48, and a part of the chassis 41 about the waist opening 36 as shown in FIGS. 6 and 7. Preferably, elasticized waist bands 50 are provided in both the front region 26 and the back region 28. The continuous belt 38 acts to dynamically create fitment forces in the pull-on garment 20 or 120 when positioned on the wearer, to maintain the pull-on garment 20 or 120 on the wearer even when loaded with body exudates thus keeping the absorbent core 25 (not shown in FIG. 7) in close proximity to the wearer, and to distribute the forces dynamically generated during wear about the waist thereby providing supplemental support for the absorbent core 25 without binding or bunching the absorbent core 25.

Figure 8:
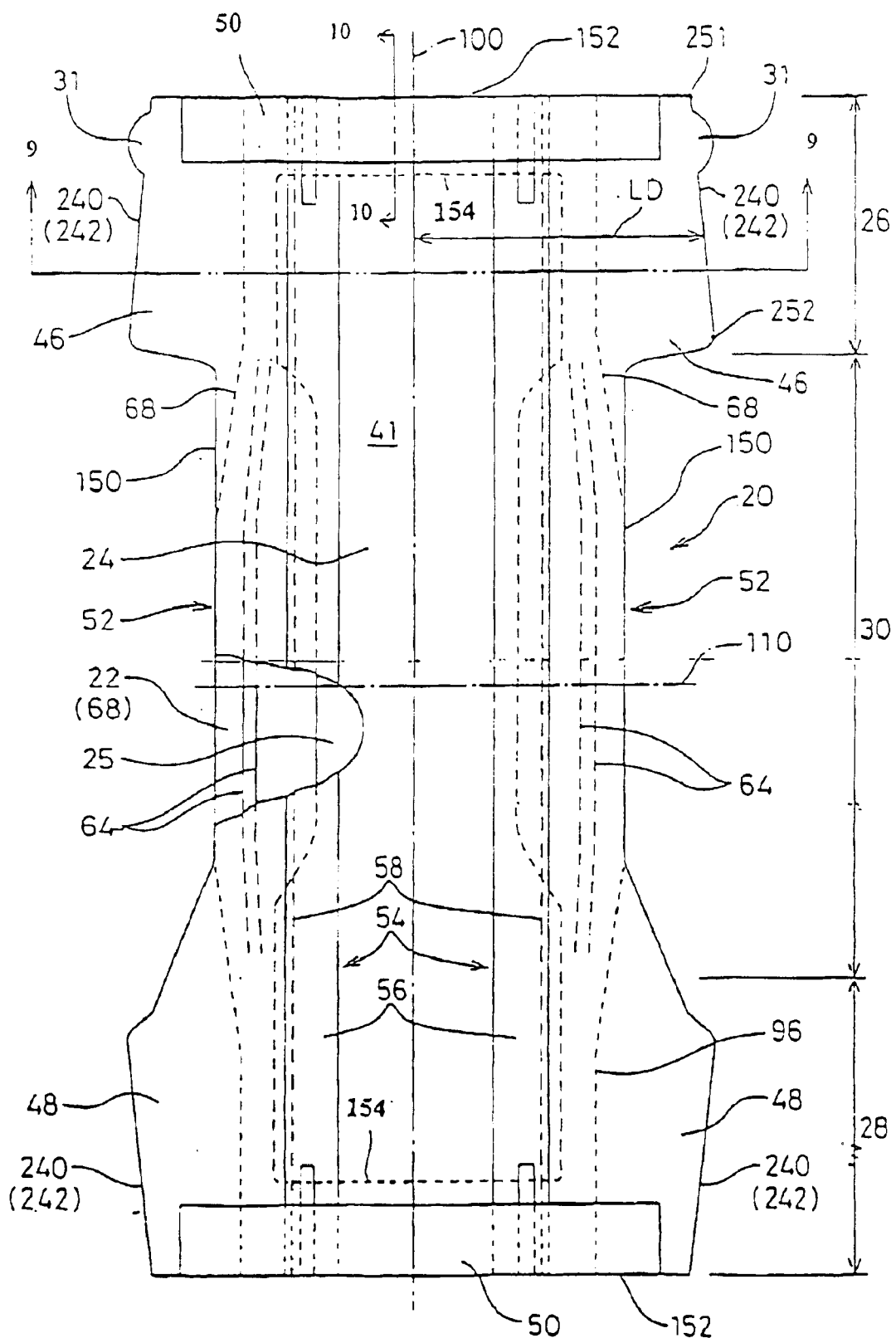
FIG. 8 is a simplified plan view of the embodiment shown in FIG. 7 in its flat uncontracted condition showing the various panels or zones of the garment.

FIG. 8 is a partially cut-away plan view of the pull-on garment 20 of FIG. 7 in its uncontracted state (except in the ear panels 46 and 48 which are left in their relaxed condition) with the topsheet 24 facing the viewer, prior to the ear panels 46 and 48 being joined together by the seams 32. The pull-on garment 20 has the front region 26, the back region 28 opposed to the front region 26, the crotch region 30 positioned between the front region 26 and the back region 28, and a periphery which is defined by the outer perimeter or edges of the pull-on garment 20 in which the side edges are designated 150 and 240, and the end edges or waist edges are designated 152. The topsheet 24 has the body-facing surface of the pull-on garment 20 which is positioned adjacent to the wearer's body during use. The backsheet 22 has the outer-facing surface of the pull-on garment 20 which is positioned away from the wearer's body. The pull-on garment 20 includes the chassis 41 including the liquid pervious topsheet 24, the liquid impervious backsheet 22 associated with the topsheet 24, and the absorbent core 25 positioned between the topsheet 24 and the backsheet 22. The garment 20 further includes the front and back ear panels 46 and 48 extending laterally outward from the chassis 41, the elasticized leg cuffs 52, and the elasticized waistbands 50. The topsheet 24 and the backsheet 22 have length and width dimensions generally larger than those of the absorbent core 25. The topsheet 24 and the backsheet 22 extend beyond the edges of the absorbent core 25 to thereby form the side edges 150 and the waist edges 152 of the garment 20. The liquid impervious backsheet 22 preferably includes a liquid impervious plastic film 68.

The pull-on garment 20 also has two centerlines, a longitudinal centerline 100 and a transverse centerline 110. Herein, "longitudinal" refers to a line, axis, or direction in the plane of the pull-on garment 20 that is generally aligned with (e.g. approximately parallel with) a vertical plane which bisects a standing wearer into left and right halves when the pull-on garment 20 is worn. Herein, "transverse" and "lateral" are interchangeable and refer to a line, axis or direction which lies within the plane of the pull-on garment that is generally perpendicular to the longitudinal direction (which divides the wearer into front and back body halves). The pull-on garment 20 and component materials thereof also have a body-facing surface which faces the skin of wearer in use and an outer-facing surface which is the opposite surface to the body-facing surface.

Each of the ear panels 45, 46 and 48 has the outermost edge line 242. Herein, "edge line" refers to lines which define the outlines of the ear panels 45, 46 and 48 or the chassis 41. Herein, "outermost" refers to portions which are farthest from the longitudinal centerline 100. At least one of the edge lines 242 has a nonuniform lateral distance LD from the longitudinal center line 100 in the uncontracted state of the garment 20.

While the topsheet 24, the backsheet 22, and the absorbent core 25 may be assembled in a variety of well known configurations, exemplary chassis configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

Figure 9:
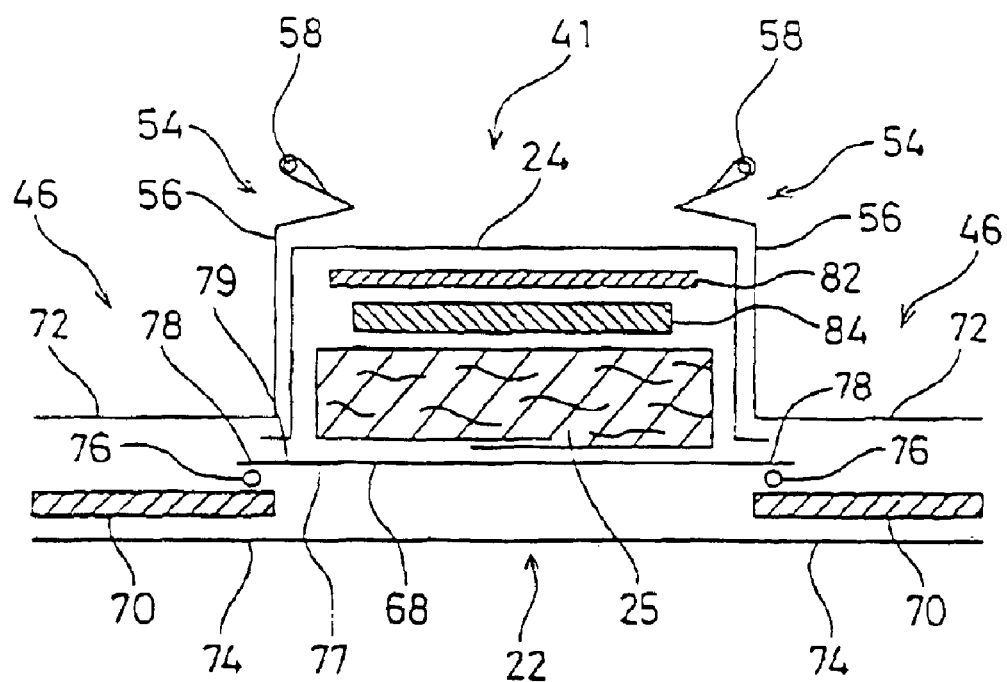
FIG. 9 is a cross-sectional view of a preferred embodiment taken along the section line 9—9 of FIG. 8.

FIG. 9 is a cross-sectional view of a preferred embodiment taken along the section line 9—9 of FIG. 8. The pull-on garment 20 includes the chassis 41 including the liquid pervious topsheet 24, the liquid impervious backsheet 22 associated with the topsheet 24, and the absorbent core 25 positioned between the topsheet 24 and the backsheet 22. The pull-on garment further includes the front ear panels 46 each extending laterally outward from the chassis 41, and an inner barrier cuffs 54. Although FIG. 9 depicts only the structure of the front ear panel 46 and the chassis 41 in the front region 26, preferably a similar structure is also provided in the back region 28. In a preferred embodiment, each of the front ear panels 46 is formed by a lamination of an extended part 72 of the barrier flap 56, an elastic laminate 70 and the nonwoven outer cover 74. The elastic laminate 70 includes a plane elastomeric material 124 (not shown in FIG. 9 but in FIG. 11). Herein, "plane elastomeric material" refers to elastomeric materials which continuously extend in two dimensional directions. Preferred plane elastomeric materials include a scrim, a perforated (or apertures formed) film, an elastomeric woven or nonwoven, and the like. In a preferred embodiment, the plane elastomeric material 124 includes at least a portion that has a nonuniform lateral width.

The absorbent core 25 can be any absorbent member which is generally compressible, conformable, non-irritating to the wearer's skin, and capable of absorbing and retaining liquids such as urine and other certain body exudates. The absorbent core 25 may be manufactured in a wide variety of sizes and shapes (e.g., rectangular, hourglass, "T"-shaped, asymmetric, etc.) and from a wide variety of liquid-absorbent materials commonly used in disposable pull-on garments and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 may vary (e.g., the absorbent core 25 may have varying caliper zones, a hydrophilic gradient, a superabsorbent gradient, or lower average density and lower average basis weight acquisition zones; or may include one or more layers or structures). Further, the size and absorbent capacity of the absorbent core 25 may also be varied to accommodate wearers ranging from infants through adults. However, the total absorbent capacity of the absorbent core 25 should be compatible with the design loading and the intended use of the garment 20.

A preferred embodiment of the garment 20 has an asymmetric, modified hourglass-shaped absorbent core 25 having ears in the front and back waist regions 26 and 28. Other exemplary absorbent structures for use as the absorbent core 25 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989.

The chassis 41 may further include an acquisition/distribution core 84 of chemically stiffened fibers positioned over the absorbent core 25, thereby forming a dual core system. In a preferred embodiment, the fibers are hydrophilic chemically stiffened cellulosic fibers. Herein, "chemically stiffened fibers" means any fibers which have been stiffened by chemical means to increase stiffness of the fibers under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains.

The fibers utilized in the acquisition/distribution core 84 can also be stiffened by means of chemical reaction. For example, crosslinking agents can be applied to the fibers which, subsequent to application, are caused to chemically form intrafiber crosslink bonds. These crosslink bonds can increase stiffness of the fibers. Whereas the utilization of intrafiber crosslink bonds to chemically stiffen the fibers is preferred, it is not meant to exclude other types of reactions for chemical stiffening of the fibers.

In the more preferred stiffened fibers, chemical processing includes intrafiber crosslinking with crosslinking agents while such fibers are in a relatively dehydrated, defibrated (i.e. individualized), twisted, curled condition. Suitable chemical stiffening agents include monomeric crosslinking agents including, but not limited to, $C_2$-$C_8$ dialdehydes and $C_2$-$C_8$ monoaldehydes having an acid functionality can be employed to form the cosslinking solution. These compounds are capable of reacting with at least two hydroxyl groups in a single cellulose chain or on proximately located cellulose chains in a single fiber. Such crosslinking agents contemplated for use in preparing the stiffened cellulose fibers include, but are not limited to, glutaraldehyde, glyoxal, formaldehyde, and glyoxylic acid. Other suitable stiffening agents are polycarboxylates, such as citric acid. The polycarboxylic stiffening agents and a process for making stiffened fibers from them are described in U.S. Pat. No. 5,190,563, entitled "Process for Preparing Individualized, Polycarboxylic Acid crosslinked Fibers" issued to Herron, on Mar. 2, 1993. The effect of crosslinking under these conditions is to form fibers which are stiffened and which tend to retain their twisted, curled configuration during use in the absorbent articles herein. Such fibers, and processes for making them are cited in the above incorporated patents.

Preferred dual core systems are disclosed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. In a preferred embodiment, the acquisition/distribution core 84 includes chemically treated stiffened cellulosic fiber material, available from Weyerhaeuser Co. (U.S.A.) under the trade designation of "CMC". Preferably, the acquisition/distribution core 84 has a basis weight of from about 40 $g/m^2$ to about 400 $g/m^2$, more preferably from about 75 $g/m^2$ to about 300 $g/m^2$.

More preferably, the chassis 22 further includes an acquisition/distribution layer 82 between the topsheet 24 and the acquisition/distribution core 84 as shown in FIG. 9. The acquisition/distribution layer 82 is provided to help reduce the tendency for surface wetness of the topsheet 24. The acquisition/distribution layer 82 preferably includes carded, resin bonded hiloft nonwoven materials such as, for example, available as Code No. FT-6860 from Polymer Group, Inc., North America (Landisiville, New Jersey, U.S.A.), which is made of polyethylene telephthalate fibers of 6 dtex, and has a basis weight of about 43 $g/m^2$. A preferable example for the acquisition/distribution layer 82 and the acquisition/distribution core 84 is disclosed in EP 0797968A1 (Kurt et al.) published on Oct. 1, 1997.

The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be included of natural fibers (e.g., wool or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 25 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991.

In a preferred embodiment, the topsheet 24 is a nonwoven web that can provide reduced tendency for surface wetness; and consequently facilitate maintaining urine absorbed by the core 25 away from the user's skin, after wetting. One of the preferred topsheet materials is a thermobonded carded web which is available as Code No. P-8 from Fiberweb North America, Inc. (Simpsonville, South Carolina, U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another preferred topsheet material is a thermobonded carded web which is available as Code No. Profleece Style 040018007 from Amoco Fabrics, Inc. (Gronau, Germany).

Another preferred topsheet 24 includes an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", issued to Thompson on Dec. 30, 1975; U.S. Pat. No. 4,324,246 entitled "Disposable Absorbent Article Having A Stain Resistant Topsheet", issued to Mullane, et al. on Apr. 13, 1982; U.S. Pat. No. 4,342,314 entitled "Resilient Plastic Web Exhibiting Fiber-Like Properties", issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", issued to Ahr et al. on Jul. 31, 1984; and U.S. Pat. No. 5,006,394 "Multilayer Polymeric Film" issued to Baird on Apr. 9, 1991.

In a preferred embodiment, the backsheet 22 includes the liquid impervious film 68 as shown in, for example, FIG. 9. Preferably, the liquid impervious film 68 longitudinally extends in the front, back and crotch regions 26, 28 and 30. More preferably, the liquid impervious film 68 does not laterally extend into the at least one of the ear panels 46 or 48. The liquid impervious film 68 has a body-facing surface 79 and an outer-facing surface 77. The liquid impervious film 68 is impervious to liquids (e.g., urine) and is preferably manufactured from a thin plastic film. However, more preferably the plastic film permits vapors to escape from the garment 20. In a preferred embodiment, a microporous polyethylene film is used for the liquid impervious film 68. A suitable microporous polyethylene film is manufactured by Mitsui Toatsu Chemicals, Inc., Nagoya, Japan and marketed in the trade as PG-P. In a preferred embodiment, a disposable tape (not shown in Figs.) is additionally joined to the outer surface of the backsheet 22 to provide a convenient disposal after soiling.

A suitable material for the liquid impervious film 68 is a thermoplastic film having a thickness of from about 0.012 mm (0.5 mil) to about 0.051 mm (2.0 mils), preferably including polyethylene or polypropylene. Preferably, the liquid impervious film has a basis weight of from about 5 $g/m^2$ to about 35 $g/m^2$. However, it should be noted that other flexible liquid impervious materials may be used. Herein, "flexible" refers to materials which are compliant and which will readily conform to the general shape and contours of the wearer's body.

Preferably, the backsheet 22 further includes the nonwoven outer cover 74 which is joined with the outer-facing surface of the liquid impervious film 68 to form a laminate (i.e., the backsheet 22). The nonwoven outer cover 74 is positioned at the outermost portion of the garment 20 and covers at least a portion of the outermost portion of the garment 20. In a preferred embodiment, the nonwoven outer cover 74 covers almost all of the area of the outermost portion of the garment 20. The nonwoven outer cover 74 may be joined to the liquid impervious film 68 by any suitable attachment means known in the art. For example, the nonwoven outer cover 74 may be secured to the liquid impervious film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

In a preferred embodiment, the nonwoven outer cover 74 is a carded nonwoven web, for example, obtainable from Havix Co., LTD., Gifu, Japan as E-2341. The nonwoven outer cover 74 is made of bi-component fibers of a polyethylene (PE) and a polypropylene (PP). The ratio of PE/PP is about 50/50. The PE/PP bi-component fiber has the dimension of 2d×51 mm. Another preferred carded nonwoven web is obtainable from Chisso Corp., Moriyama, Japan. The nonwoven outer cover 74 is also made of bi-component fibers of a polyethylene (PE) and a polypropylene (PP). The ratio of PE/PP is about 50/50.

In another preferred embodiment, the nonwoven web is a spunbonded nonwoven web, for example, obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PE/PP bi-component fiber has the thickness is approximately 2.3d. Another spunbonded nonwoven web is obtainable from Fiberweb France S. A., under Code No. 13561 DAPP.

The backsheet 22 is preferably positioned adjacent the outer-facing surface of the absorbent core 25 and is preferably joined thereto by any suitable attachment means known in the art. For example, the backsheet 22 may be secured to the absorbent core 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn., U.S.A., and marketed as HL-1358J. An example of a suitable attachment means including an open pattern network of filaments of adhesive is disclosed in U.S. Pat. No. 4,573,986 entitled "Disposable Waste-Containment Garment", which issued to Minetola et al. on Mar. 4, 1986. Another suitable attachment means including several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may include heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front region 26 and the back region 28.

The pull-on garment 20 preferably further includes elasticized leg cuffs 52 for providing improved containment of liquids and other body exudates. The elasticized leg cuffs 52 may include several different embodiments for reducing the leakage of body exudates in the leg regions. (The leg cuffs can be and are sometimes also referred to as leg bands, side flaps, barrier cuffs, elastic cuffs or gasketing cuffs.) U.S. Pat. No. 3,860,003 entitled "Contractable Side Portions for Disposable Diaper" issued to Buell on Jan. 14, 1975, describes a disposable diaper which provides a contractible leg opening having a side flap and one or more elastic members to provide an elasticized leg cuff. U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

While each elasticized leg cuff 52 may be configured so as to be similar to any of the leg bands, side flaps, barrier cuffs, or elastic cuffs described above, it is preferred that the elasticized leg cuff 52 includes an elastic gasketing cuff 62 with one or more elastic strands 64 as shown in FIG. 8, which is described in the above-referred U.S. Pat. Nos. 4,695,278 and 4,795,454. It is also preferred that each elasticized leg cuff 52 further includes inner barrier cuffs 54 each including a barrier flap 56 and a spacing means 58 which are described in the above-referenced U.S. Pat. No. 4,909,803.

The pull-on garment 20 of the present invention further includes an elasticized waistband 50 that provides improved fit and containment. The elasticized waistband 50 is that portion or zone of the pull-on garment 20 which is intended to elastically expand and contract to dynamically fit the wearer's waist. The waistband 50 of the present invention includes an elastic laminate 70 which will be described in detail hereinafter. The waistband 50 is disposed along at least one, preferably both of the end edges 152 of the disposable garment 20. The elasticized waistband 50 preferably extends longitudinally inwardly from the end edge 152 of the pull-on garment 20 toward the waist edge 154 of the absorbent core 25. Preferably, the pull-on garment 20 has two elasticized waistbands 50, one positioned in the back region 28 and one positioned in the front region 26, although other pull-on diaper embodiments can be constructed with a single elasticized waistband. The elasticized waistband 50 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell.

Figure 10:
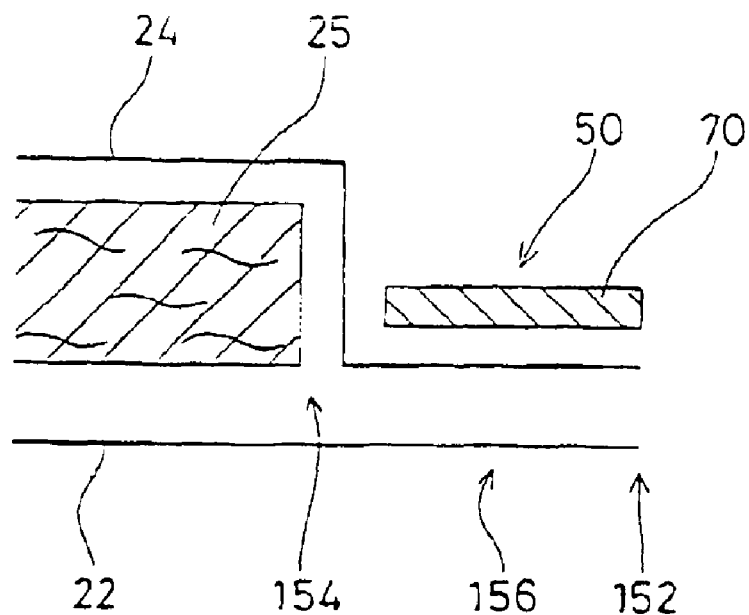
FIG. 10 is a cross-sectional view of a waistband 50 of a preferred embodiment taken along the section line 10—10 of FIG. 8.
Figure 11:
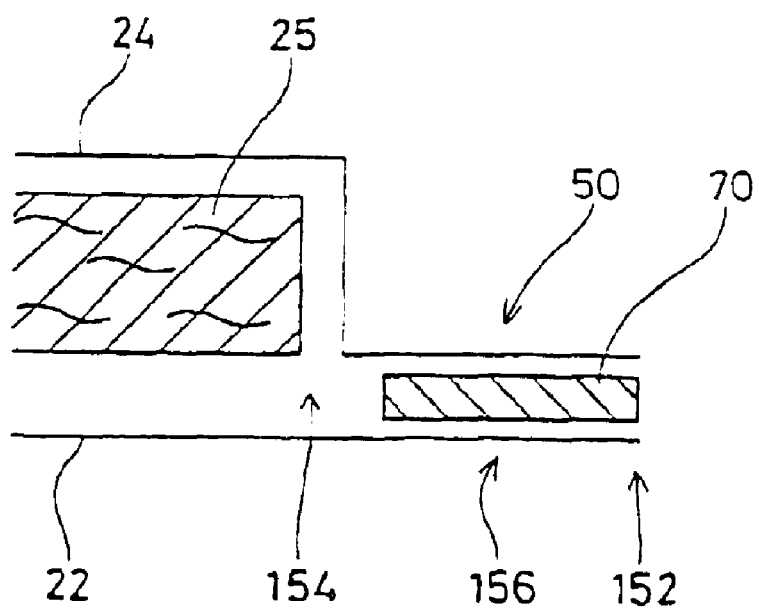
FIG. 11 is a cross-sectional view of a waistband 50 of another preferred embodiment.
Figure 12:
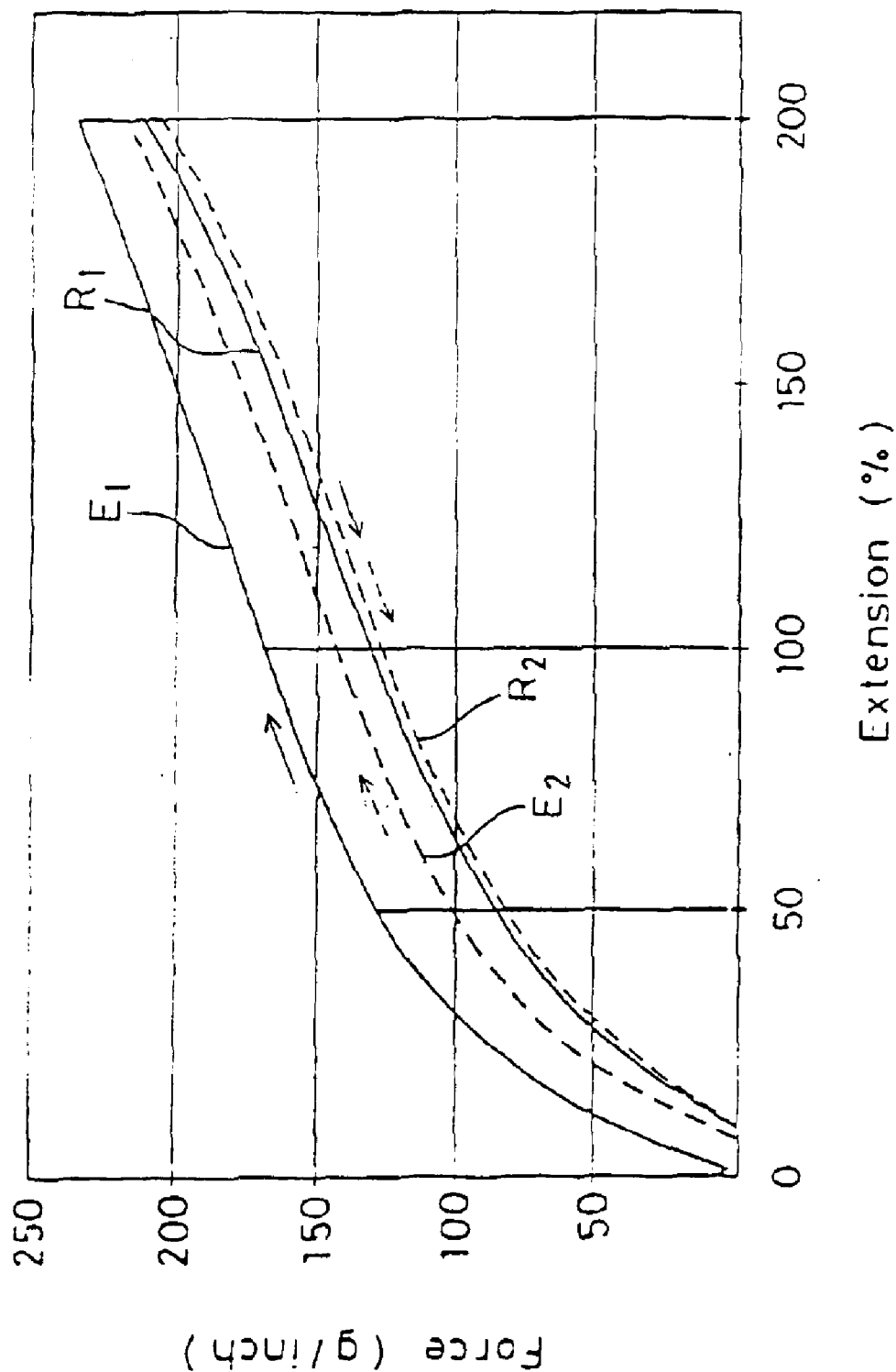
FIG. 12 is a graph showing the two-cycles of hysteresis curves of an elastomeric material, in a preferred embodiment.

FIG. 10 is a cross-sectional view of one preferred embodiment taken along the section line 10—10 of FIG. 8. As shown in FIG. 10, both the backsheet 22 and the topsheet 24 extend beyond the waist edge 154 of the absorbent core 25 to define a waist flap 156. Preferably, the juxtaposed areas of the backsheet 22 and the topsheet 24 are joined together by an adhesive (not shown in Figs.). In a preferred embodiment, the waistband 50 is joined to the waist flap 156. Preferably, the waistband 50 is disposed on and joined to the topsheet 24 as shown in FIG. 10. Alternatively, the waistband 50 can be disposed and joined between the backsheet 22 and the topsheet 24 as shown in FIG. 11. The waistband 50 can be joined to the topsheet 24 (and the backsheet 22) by an adhesive means (not shown in Figs.) such as those well known in the art. For example, the waistband 50 may be secured to the waist flap 156 by a uniform continuous layer of adhesive, a patterned layer of adhesive, or an array of separate lines or spots of adhesive. A preferred adhesive for use is available from Ato Findley Inc., WI, U.S.A., under the designation H2085.

In a preferred embodiment, the waistband 50 is secured to the waist flap 156 in an elastically contractible condition so that in a normally unrestrained configuration the waistband 50 effectively contract or gather the waist flap 156. The waistband 50 can be secured to the waist flap 156 in an elastically contractible condition in at least two ways. For example, the waistband 50 may be stretched and secured to the waist flap 156 while the waist flap 156 is in an uncontracted condition. Alternatively, the waist flap 156 may be contracted, for example by pleating, and the waistband 50 is secured to the contracted waist flap 156 while the waistband 50 in its relaxed or unstretched condition.

Yet alternatively, the waistband 50 is joined, in its relaxed or unstretched condition, to the waist flap 156 which is in an uncontracted condition, thereby forming a composite laminate with the materials of the backsheet 22 and the topsheet 24. At least a portion, preferably the entire portion of the composite laminate is then subjected to mechanical stretching sufficient to permanently elongate the non-elastic components which are the backsheet 22 and the topsheet 24. The composite laminate is then allowed to return to its substantially untensioned condition. Thus, the composite laminate is formed into a "zero strain" stretch laminate which works as elasticized waistband 50.

Herein, "zero strain" stretch laminate refers to a laminate included of at least two plies of material which are secured to one another along at least a portion of their coextensive surfaces while in a substantially untensioned ("zero strain") condition; one of the plies including a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Particularly preferred methods and apparatus used for making stretch laminates utilize meshing corrugated rolls to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992.

In a preferred embodiment, the waistband 50 extends across essentially the entire lateral width of the absorbent core 25. Herein, "lateral width" refers to the dimension between the side edges of components of disposable garments. Herein, "across essentially" is used in this context to indicate that the waistband 50 does not need to extend absolutely across the entire width of the absorbent core 25 so long as it extends sufficiently far across the width thereof to provide the elasticized waistband. Preferably, the waistband 50 extends across only a portion of the lateral width of the absorbent core 25, more preferably at least between portions in the ear panels 46 and 48 (as shown in FIG. 8). In one preferred embodiment, the waistband 50 extends across the entire lateral width of the garment 20 (not shown Figs.).

The extent to which the waistband 50 extends inboard from the end edge 152 of the garment 20, and thus the longitudinal span of the resultant waistband, can vary according to the particular construction of the garment 20. The longitudinal span of the waistband 50 is at least about 5 mm, preferably from about 6 mm to about 60 mm, more preferably from about 15 mm to about 30 mm.

At least one of the ear panels 45, 46 and 48 includes the elastic laminate 70 of the present invention. For example, each of the front ear panels 46 shown in FIG. 9 includes the elastic laminate 70 which includes the elastomeric material 124 (not shown in FIG. 9) which preferably extends laterally outward from the chassis 41 to provide good fitness by generating the optimal retention (or sustained) force at the waist and side areas of the wearer. Preferably, the elastomeric material 124 is extensible in at least one direction, preferably in the lateral direction to generate a retention (or sustained) force that is optimal to prevent the pull-on garment 20 from drooping, sagging, or sliding down from its position on the torso without causing the red marking on the skin of the wearer. In a preferred embodiment, each of the ear panels 45, 46 and 48 includes the elastomeric material 124.

The elastic laminate 70 is operatively joined to at least one of the nonwoven webs 72 and 74 in the ear panels 45, 46 and 48 to allow the elastic laminate 70 to be elastically extensible in at least the lateral direction. In a preferred embodiment, the elastic laminate 70 is operatively joined to the nonwoven webs 72 and 74 by securing them to at least one, preferably both of the nonwoven webs 72 and 74 while in a substantially untensioned (zero strain) condition.

The elastic laminate 70 can be operatively joined to the nonwoven webs 72 and 74, by using either an intermittent bonding configuration or a substantially continuous bonding configuration. Herein, "intermittently" bonded laminate web means a laminate web wherein the plies are initially bonded to one another at discrete spaced apart points or a laminate web wherein the plies are substantially unbonded to one another at discrete spaced apart areas. Conversely, a "substantially continuously" bonded laminate web means a laminate web wherein the plies are initially bonded substantially continuously to one another throughout the areas of interface. It is preferred that the stretch laminate be bonded over all or a significant portion of the stretch laminate so that the inelastic webs (i.e., the nonwoven webs 72 and 74) elongate or draw without causing rupture, and the layers of the stretch laminates are preferably bonded in a configuration that maintains all of the layers of the stretch laminate in relatively close adherence to one another after the incremental mechanical stretching operation. Consequently, the elastic panel members and the other plies of the stretch laminate are preferably substantially continuously bonded together using an adhesive. In a particularly preferred embodiment, the adhesive selected is applied with a control coat spray pattern at a basis weight of about 7.0 grams/square m. The adhesive pattern width is about 6.0 cm. The adhesive is preferably an adhesive such as is available from Nitta Findley Co., Ltd., Osaka, Japan, under the designation H2085F. Alternatively, the elastic panel member and any other components of the stretch laminates may be intermittently or continuously bonded to one another using heat bonding, pressure bonding, ultrasonic bonding, dynamic mechanical bonding, or any other method as is known in the art.

After the elastic laminate 70 is operatively joined to at least one of the nonwoven webs 72 and 74, at least a portion of the resultant composite stretch laminate is then subjected to mechanical stretching sufficient to permanently elongate the non-elastic components which are, for example, the nonwoven webs 72 and 74. The composite stretch laminate is then allowed to return to its substantially untensioned condition. At least one pair of, preferably both of the ear panels 45, 46 and 48 is thus formed into "zero strain" stretch laminates. (Alternatively, the elastic laminate 70 could be operatively joined in a tensioned condition and then subjected to mechanical stretching; although this is not as preferred as a "zero strain" stretch laminate.)

The elastic laminate 70 is preferably joined to, more preferably directly secured to the respective edges 78 of the liquid impervious film (i.e., the liquid impervious film 68) through an adhesive 76 as shown in FIG. 9. In a preferred embodiment, while liquid impervious film 68 longitudinally extends in the front, back and crotch regions 26, 28 and 30, it does not laterally extend into at least one of, preferably each of the extensible ear panels 45, 46 and 48. In a more preferred embodiment, the elastic laminate 70 is joined to the respective edges 78 of the liquid impervious film 68 at the outer-facing surface 77 as shown in FIG. 9. In an alternative embodiment, the elastic laminate 70 may be joined to the respective edges 78 of the liquid impervious film 68 at the body-facing surface 79 (not shown in Figs.). Preferably, the adhesive 76 is applied in a spiral glue pattern. In a preferred embodiment, the adhesive 76 is a flexible adhesive with an amorphous and crystallizing component. Such a preferred adhesive is made by Nitta Findley Co., Ltd., Osaka, Japan, under the designation H2085F. Alternatively, the elastic laminate 70 may be joined to the respective edges 78 of the liquid impervious film 68 by any other bonding means known in the art which include heat bonds, pressure bonds, ultrasonic bonds, dynamic mechanical bonds, or combinations of these attachment means.

It is understood that the examples and embodiments described herein are for illustrative purpose only and that various modifications or changes will be suggested to one skilled in the art without departing from the scope of the present invention.

What is claimed is:

1. An elastic laminate elastically extensible in at least one direction, comprising:
   (a) an elastomeric layer having a first surface and a second surface opposing the first surface; wherein the elastomeric layer is in a form selected from the group consisting of a scrim, an apertures formed film, an elastomeric woven or nonwoven, discrete strands and strings;
   wherein the elastomeric woven or nonwoven and discrete strand and strings comprise a polystyrene thermoplastic elastomer selected from the group consisting of a styrene-butadiene-styrene thermoplastic elastomer, a styrene-isoprene-styrene thermoplastic elastomer, a styrene-ethylene/butylene-styrene thermoplastic elastomer, a styrene-ethylene/propylene-styrene thermoplastic elastomer, a styrene-ethylene/propylene thermoplastic elastomer, a hydrogenated styrene butadiene rubber, and a mixture thereof; and
   (b) a first nonwoven layer joined to the first surface of the elastomeric layer, the first nonwoven layer being formed from component fibers having a primary fiber direction;
   wherein the first nonwoven layer has a Fiber Orientation Ratio within about ±20 degrees from a primary fiber direction of at least about 65%;
   wherein the elastic laminate exhibits elasticity without mechanical stretching of the first nonwoven layer during manufacture.

2. The elastic laminate according to claim 1, wherein the first nonwoven layer has a Tensile Strength Ratio of at least about 15.

3. The elastic laminate of claim 1, wherein the first nonwoven layer has a stress of less than about 200 gf/inch (about 80 gf/cm) at 30% elongation.

4. The elastic laminate of claim 1, wherein the first nonwoven layer has a Fiber Orientation Ratio within about ±10 degrees from the primary fiber direction of at least about 45%.

5. The elastic laminate of claim 1, wherein the first nonwoven layer has a basis weight of less than about 60 g/m².

6. The elastic laminate of claim 1, further comprising a second nonwoven layer joined to the second surface of the elastomeric material.

7. The elastic laminate of claim 1, wherein the first nonwoven layer is made from synthetic continuous fibers.

8. The elastic laminate of claim 7, wherein the synthetic continuous fibers are made from a polyolefin or a polyester.

9. The elastic laminate of claim 7, wherein the synthetic continuous fibers are bicomponent fibers.

10. A disposable garment having a front region, a back region and a crotch region between the front region and the back region, comprising: a chassis provided in the front, back and crotch regions and having edge lines in the front and back regions, the chassis comprising a liquid pervious topsheet, a liquid impervious backsheet associated with the topsheet, and an absorbent core disposed between the topsheet and the backsheet; and at east one pair of extensible side panels extending laterally outward from the chassis in the font or back region, wherein at least one of the side panels including an elastic laminate elastically extensible at least in the lateral direction, the elastic laminate including;
   (a) an elastomeric layer having a first surface and a second surface opposing the first surface; wherein the elastomeric layer is in a form selected from the group consisting of a scrim, an apertures formed film, an elastomeric woven or nonwoven, discrete strands and strings;
   wherein the elastomeric woven or nonwoven and discrete strand and strings comprise a polystyrene thermoplastic elastomer selected from the group consisting of a styrene-butadiene-styrene thermoplastic elastomer, a styrene-isoprene-styrene thermoplastic elastomer, a styrene-ethylene-butylene-styrene thermoplastic elastomer, a styrene-ethylene/propylene-styrene thermoplastic elastomer, a styrene-ethylene/propylene thermoplastic elastomer, a hydrogenated styrene butadiene rubber, and a mixture thereof; and
   (b) a first nonwoven layer joined to the first surface of the elastomeric layer, the first nonwoven layer being formed from component fibers having a primary fiber direction;
   wherein the first nonwoven layer has a Fiber Orientation Ratio within about ±20 degrees from a primary fiber direction of at least about 65%;
   wherein the elastic laminate exhibits elasticity without mechanical stretching of the first nonwoven layer during manufacture.

11. A disposable garment having a longitudinal center line, longitudinal edges, end edges, a front region, a back region and a crotch region between the front region and the back region, comprising: a chassis provided in the front, back and crotch regions and having edge lines in the front and back regions, the chassis comprising a liquid pervious topsheet, a liquid impervious backsheet associated with the topsheet, and an absorbent core disposed between the topsheet and the backsheet; and a waistband disposed along at least one of the end edges of the disposable garment, wherein the waistband includes an elastic laminate including
   (a) an elastomeric layer having a first surface and a second surface opposing the first surface; wherein the elastomeric layer is in a form selected from the group consisting of a scrim, an apertures formed film, an elastomeric woven or nonwoven, discrete strands and strings;
   wherein the elastomeric woven or nonwoven and discrete strands and strings comprise a polystyrene thermoplastic elastomer selected from the group consisting of a styrene-butadiene-styrene thermoplastic elastomer, a styrene-isoprene-styrene thermoplastic elastomer, a styrene-ethylene/butylene-styrene thermoplastic elastomer, a styrene-ethylene/propylene-styrene thermoplastic elastomer, a styrene-ethylene/propylene thermoplastic elastomer, a hydrogenated styrene butadiene rubber, and a mixture thereof; and
   (b) a first nonwoven layer joined to the first surface of the elastomeric layer, the first nonwoven layer being formed from component fibers having a primary fiber direction;
   wherein the first nonwoven layer has a Fiber Orientation Ratio within about ±20 degrees from a primary fiber direction of at least about 65%;
   wherein the elastic laminate exhibits elasticity without mechanical stretching of the first nonwoven layer during manufacture.

12. The disposable garment of claim 10, further comprising seams which join the chassis to the side panels to form two leg openings and a waist opening.

13. The disposable garment of claim 10, wherein the at least one pair of the side panels comprises one pair of extensible front side panels extending laterally outward from the chassis in the front region, and one pair of extensible back side panels extending laterally outward from the chassis in the back region, and the disposable garment further comprises seams each joining the front and back side panels to form the two leg openings and the waist opening.

14. The disposable garment of claim 10, wherein the first nonwoven layer has a Tensile Strength Ratio of at least about 15.

15. The disposable garment of claim 10, wherein the first nonwoven layer has a stress of less than about 200 gf/inch (about 80 gf/cm) at 30% elongation.

16. The disposable garment of claim 10, wherein the first nonwoven layer has a Fiber Orientation Ratio within about ±10 degrees from the primary fiber direction of at least about 45%.

17. The disposable garment of claim 10, further comprising a second nonwoven layer joined to the second surface of the elastomeric material.

18. The disposable garment of claim 10, wherein the elastomeric material is in the form of a continuous plane layer or a strand.

19. The disposable garment of claim 10, wherein the first nonwoven layer is formed from synthetic continuous fibers which are made from a polyolefin or a polyester.

* * * * *

UNITED STATES PATENT AND TRADEMARK OFFICE
CERTIFICATE OF CORRECTION

PATENT NO. : 6,878,647 B1 Page 1 of 1
APPLICATION NO. : 09/806047
DATED : April 12, 2005
INVENTOR(S) : Ebrahim Rezai et al.

It is certified that error appears in the above-identified patent and that said Letters Patent is hereby corrected as shown below:

Item [74]
In the listing of the Attorney, Agent of Firm, delete "Dare M. Kendall" and insert therefore -- Dara M. Kendall--.

Column 2, line 7 of the issued patent, delete "easily shred or tom" and insert therefor --easily shred or torn--.

Signed and Sealed this

Twenty-second Day of August, 2006

JON W. DUDAS
*Director of the United States Patent and Trademark Office*